United States Patent [19]
Barbut et al.

[11] Patent Number: 5,662,671
[45] Date of Patent: Sep. 2, 1997

[54] ATHERECTOMY DEVICE HAVING TRAPPING AND EXCISING MEANS FOR REMOVAL OF PLAQUE FROM THE AORTA AND OTHER ARTERIES

[75] Inventors: Denise Barbut, New York, N.Y.; Jonathan D. Root, San Francisco, Calif.; Robert Rizzari, Haverhill, Mass.; James M. Sellers, Hampstead, N.H.; Giovanni Pastrone, Los Gatos; John McKenzie, San Carlos, both of Calif.

[73] Assignee: Embol-X, Inc., Portola Valley, Calif.

[21] Appl. No.: 683,503

[22] Filed: Jul. 17, 1996

[51] Int. Cl.$^6$ .................................................. A61M 25/00
[52] U.S. Cl. ...................... 606/170; 606/159; 604/22; 604/104
[58] Field of Search ........................ 606/170, 159, 606/194; 604/22, 104–107, 95, 96, 268; 128/660, 341–344, 325

[56] References Cited

U.S. PATENT DOCUMENTS

| Re. 33,569 | 4/1991 | Gifford, III et al. | 606/159 |
|---|---|---|---|
| 3,889,657 | 6/1975 | Baumgarten | 128/2 |
| 4,631,052 | 12/1986 | Kensey | 604/22 |
| 4,723,549 | 2/1988 | Wholey et al. | 128/344 |
| 4,790,812 | 12/1988 | Hawkins, Jr. et al. | 604/22 |
| 4,794,928 | 1/1989 | Kletschka | 128/344 |
| 4,794,931 | 1/1989 | Yock | 128/660 |
| 4,857,045 | 8/1989 | Rydell | 604/22 |
| 4,857,046 | 8/1989 | Stevens et al. | 604/22 |
| 4,867,157 | 9/1989 | McGurk-Burleson et al. | 128/305 |
| 4,898,575 | 2/1990 | Fischell et al. | 604/22 |
| 4,921,484 | 5/1990 | Hillstead | 604/104 |
| 4,926,858 | 5/1990 | Gifford, III et al. | 606/159 |
| 4,950,277 | 8/1990 | Farr | 606/159 |
| 4,955,895 | 9/1990 | Sugiyama et al. | 606/194 |
| 4,957,482 | 9/1990 | Shiber | 604/22 |
| 4,979,951 | 12/1990 | Simpson | 606/159 |
| 4,986,807 | 1/1991 | Farr | 604/22 |
| 5,007,896 | 4/1991 | Shiber | 604/22 |
| 5,007,917 | 4/1991 | Evans | 606/170 |
| 5,019,088 | 5/1991 | Farr | 606/159 |
| 5,053,008 | 10/1991 | Bajaj | 604/104 |
| 5,053,044 | 10/1991 | Mueller et al. | 606/159 |
| 5,071,425 | 12/1991 | Gifford, III et al. | 606/159 |
| 5,087,265 | 2/1992 | Summers | 606/159 |
| 5,100,424 | 3/1992 | Jang et al. | 606/159 |

(List continued on next page.)

OTHER PUBLICATIONS

"The International Publication for the Study of the Heart and Circulation", American Heart Journal, Sep. 1990.
"Atherosclerotic Disease of the Aortic Arch as a Risk Factor for Recurrent Ischemic Stroke", The New England Journal of Medicine, pp. 1216–1221, May 1996.
"Catheterization and Cardiovascular Diagnosis", brochure, by Wiley-Liss Jan. 1994.
"Protruding Atheromas in the Thoracic Aortic and Systemic Embolization", pp. 423–427 American College of Physicians 1991.
"Recognition and Embolic Potential of Intraaortic Atherosclerotic Debris", American College of Cardiology Jan. 1991.

Primary Examiner—Michael Buiz
Assistant Examiner—Nancy Mulcare
Attorney, Agent, or Firm—Lyon & Lyon LLP

[57] ABSTRACT

An arterial catheter system for removing plaque from the aorta and other arteries is disclosed. The system typically includes an elongate catheter member, a filtration apparatus disposed within the distal region, and an atherectomy assembly which includes a mechanism for trapping and holding mobile or fixed plaque and an excising mechanism for removing the plaque. In use, the catheter is positioned so that the atherectomy assembly lies within a region of interest, the filtration apparatus is deployed downstream of the region of interest, the plaque is trapped and held by a snare, vacuum, or other trapping means, and then the excising mechanism is activated to remove the plaque. Methods are also disclosed for removing plaque from the aorta and other arteries.

34 Claims, 19 Drawing Sheets

U.S. PATENT DOCUMENTS

| | | | |
|---|---|---|---|
| 5,100,425 | 3/1992 | Fischell et al. | 606/159 |
| 5,135,531 | 8/1992 | Shiber | 606/159 |
| 5,318,576 | 6/1994 | Plassche, Jr. et al. | 606/159 |
| 5,366,464 | 11/1994 | Belknap | 606/159 |
| 5,409,454 | 4/1995 | Fischell et al. | 604/22 |
| 5,512,044 | 4/1996 | Duer | 604/22 |

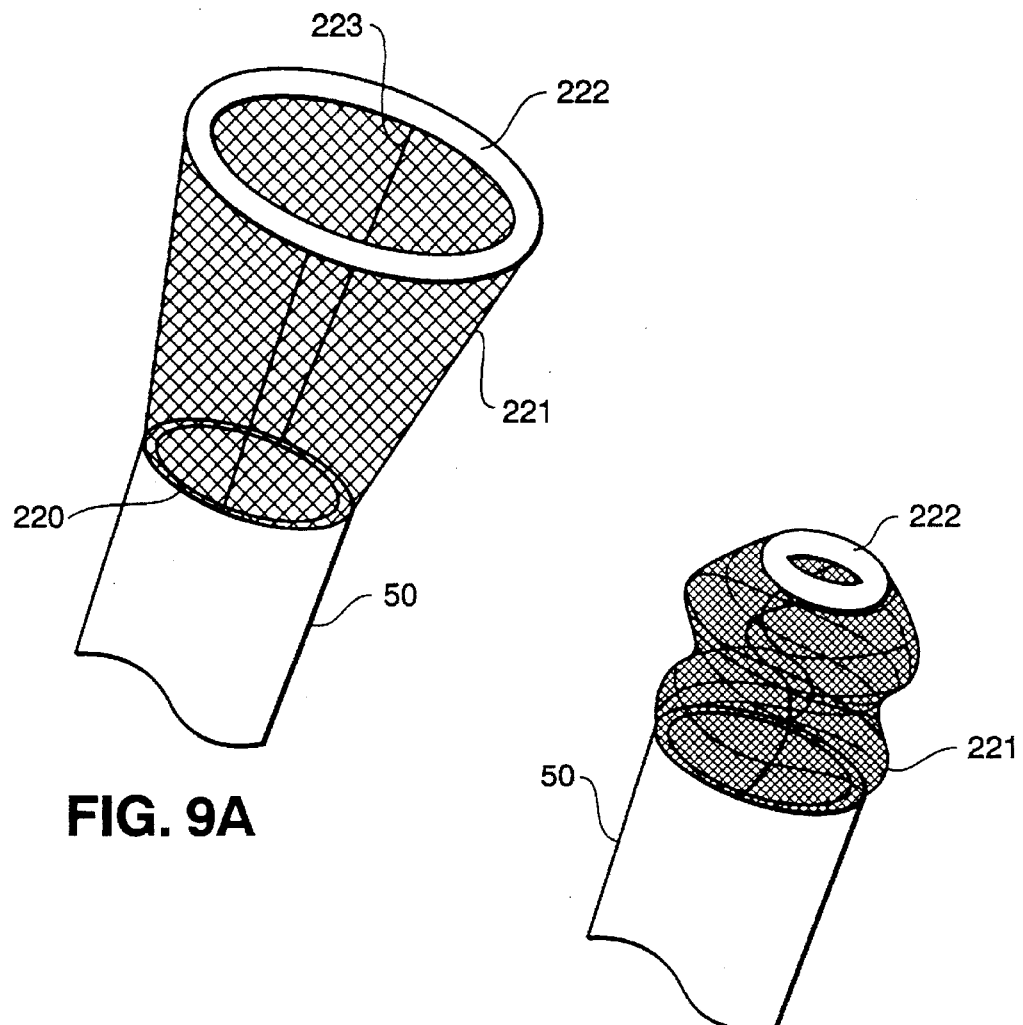
FIG. 9A
FIG. 9B
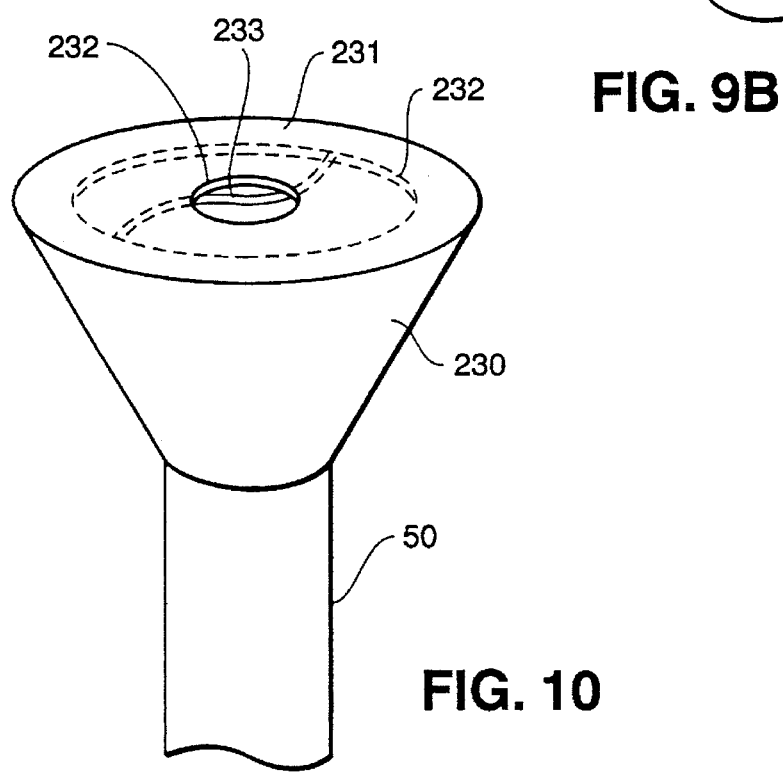
FIG. 10

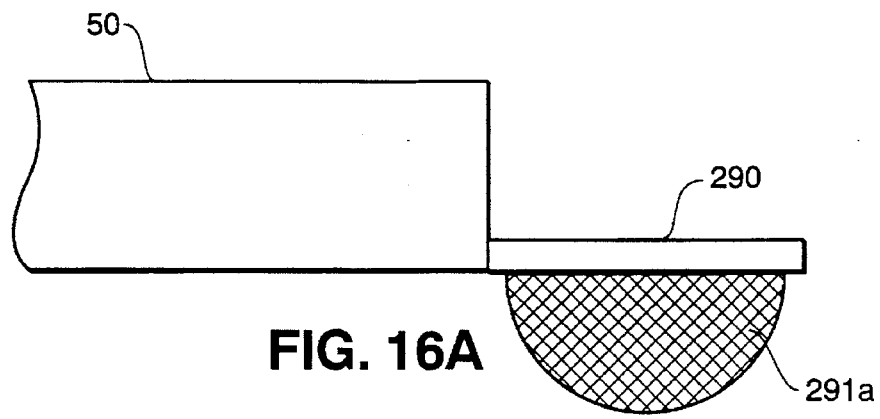
FIG. 16A
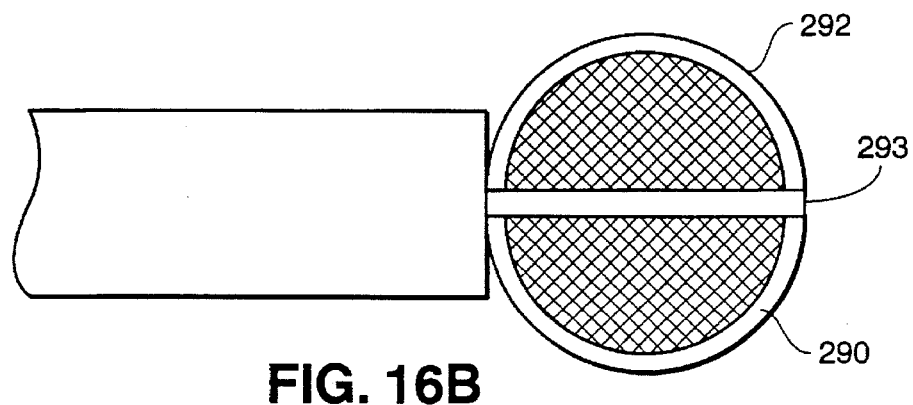
FIG. 16B
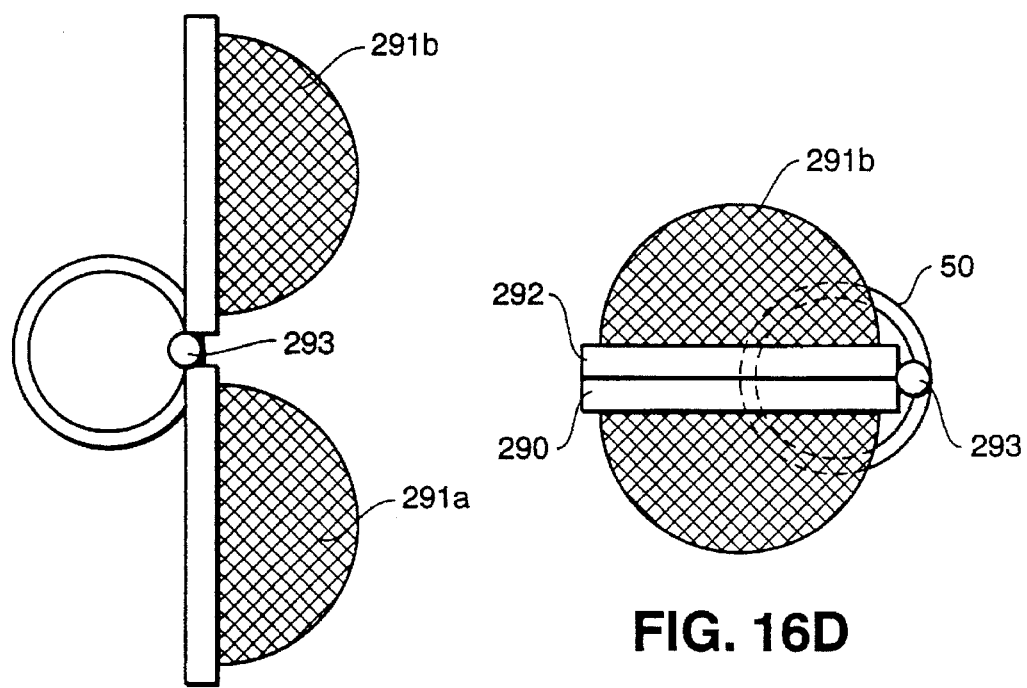
FIG. 16C
FIG. 16D

ATHERECTOMY DEVICE HAVING TRAPPING AND EXCISING MEANS FOR REMOVAL OF PLAQUE FROM THE AORTA AND OTHER ARTERIES

FIELD OF THE INVENTION

This invention relates to methods and apparatus for excising mobile and non-mobile atheromatous plaque from the aortic wall and valve and also other arteries such as the carotid arteries and femoral arteries. The devices include an atherectomy catheter system for operation in the aorta, common carotid artery, external and internal carotid arteries, brachiocephalic trunk, middle cerebral artery, anterior cerebral artery, posterior cerebral artery, vertebral artery, basilar artery, subclavian artery, brachial artery, axillary artery, iliac artery, renal artery, femoral artery, popliteal artery, celiac artery, superior mesenteric artery, inferior mesenteric artery, anterior tibial artery, posterior tibial artery and all other arteries carrying oxygenated blood, and the catheter may optionally include blood filter means which enable the capture of plaque inadvertently dislodged during an atherectomy procedure.

BACKGROUND OF THE INVENTION

The importance of the aorta as a source of emboli has only recently become apparent since the advent of transesophageal echocardiography (TEE). This technique has enabled physicians to visualize the aortic wall in great detail and to quantify atheromatous aortic plaque according to thickness, degree of intraluminal protrusion, and presence or absence of mobile components. See Katz et al., Journal of the American College of Cardiology 20:70–77 (1992), this and all other references cited herein are expressly incorporated by reference as if set forth herein in their entirety. Anecdotal reports linking embolic events to the presence of mobile aortic atheroma have lead to large-scale studies aimed at establishing the exact relationship between aortic atheromatosis and cerebral embolization. See Flory, American Journal of Pathology 21:549–565 (1945); Beal et al., Neurology 31:860–865 (1981); Soloway et al., Archives of Neurology 11:657–667 (1973); Russell et al., Stroke 22:253–258 (1991); and Tunick et al., Annals of Internal Medicine 114:391–392 (1991).

In 1992, and again in 1994, Amarenco disclosed an unequivocal association between embolic stroke and TEE-detected aortic plaque, especially in the presence of mobile plaque. See Amarenco et al., Stroke 23:1005–1009 (1992); and Amarenco et al., New England Journal of Medicine 331:1474–1479 (1994). Amarenco performed a prospective, case-control study of the frequency and thickness of atherosclerotic plaques in the ascending aorta and proximal arch in 250 patients with stroke and in 250 controls. Amarenco found protruding plaque (4 mm) in 14.4% of patients with stroke but only 2% of control. Plaques of all thickness were associated with stroke, but the association was strongest for plaques more than 4 mm in thickness. Protruding plaque was present in 28.2% of 78 patients with stroke of unknown cause, compared with 8.1% of 172 patients with stroke of known or likely causes. Furthermore, mobile plaque was present in 7.7% of patients with stroke of unknown cause, compared with only 0.6% of patients with stroke of known cause. The association between protruding atheroma and stroke was strongest for ascending aorta and proximal arch, but weaker for the distal arch and descending aortic disease.

Ulcerated aortic plaque, the pathologic correlate of TEE-detected mobile plaque, was present in autopsies of 26% of 239 patients with cerebrovascular disease as compared with 5% of 261 patients with other neurologic diseases. The prevalence of ulcerated arch lesions was 61% among 28 patients with no known causes of brain infarction, as compared with 22% among 155 patients with a known cause of infarction. See Amarenco et al., New England Journal of Medicine 326:221–225 (1992).

Amarenco and others showed prospectively (following patients for two years) a strong correlation between mobile plaque and embolic stroke or emboli to the legs and/or kidneys. In an attempt to investigate the value of aortic atheroma in predicting future vascular events, Tunick followed 42 patients with TEE-detected protruding atheroma and an equal number of controls for up to two years. See Tunick et al., Journal of the American College of Cardiology 23:1085–1090 (1994). Fourteen (33%) patients with protruding plaque had 19 embolic events, as compared with 3 out of 42 (7%) controls. These observations have been independently confirmed by a number of other recent studies on risk factors of embolic stroke. See Tunick et al., American Heart Journal 120:658–660 (1990), Karalis et al., Journal of the American College of Cardiology 17:73–78 (1991), Tunick et al., Annals of Internal Medicine 115:423–427 (1991), Tunick et al., American Heart Journal 124:239–241 (1992), Horowitz et al., Neurology 42:1602–1604 (1992), Toyoda et al., Stroke 23:1056–1061 (1992), Nihoyannopoulos et al., American Journal of Cardiology 71:1208–1212 (1993), Davila-Roman et al., Stroke 25:2010–2016 (1994), and the French Study of Aortic Plaques in Stroke Group, New England Journal of Medicine 334(19):1216–1221 (1996).

The danger of embolic stroke from atheroma present in the aorta, especially of mobile plaque, has been shown in patients undergoing cardiac surgery, and this effect is due to mechanical manipulations performed on the aorta during cardiac surgery. See Hartman, et al., Anesthesia Analgesia 1996 (in press), Gold et al., Journal of Thoracic Cardiovascular Surgery 110:1302–1314 (1995), Marshall et al., Annals of Thoracic Surgery 48:339–344 (1989), Katz et al., Journal of American College of Cardiology 20:70–77 (1992); and Hosoda et al., Journal of Cardiovascular Surgery 32:301–306 (1991). In fact, among patients undergoing coronary bypass surgery, aortic atheromatosis has emerged as the single most important factor in perioperative neurologic morbidity. See Tunick et al., Annals of Internal Medicine 114:391–392 (1991); Karalis et al., Journal of the American College of Cardiology 17:73–78 (1991); Marschall et al., Journal of Cardiothoracic Vascular Anesthesia 8:5–13 (1994); Blauth et al., Journal of Thoracic Cardiovascular Surgery 103:1104–1112 (1992); Wareing et al., Journal of Thoracic Cardiovascular Surgery 103:453–462 (1992); Ribakove et al., Annals of Thoracic Surgery 53:758–763 (1992); Brillman, Neurologic Clinics 11:475–495 (1993); and Amarenco et al., Stroke 23:1005–1009 (1992). As the number of elderly patients undergoing bypass surgery has increased, the decline in overall mortality and cardiac morbidity achieved by improvements in surgical and anesthetic techniques has been largely obscured by increasing neurologic complication rates. See Loop et al., Cleveland Clinical Journal of Medicine 55:23–24 (1988); Hill et al., Annals of Thoracic Surgery 7:409–419 (1969); Gardner et al., Annals of Thoracic Surgery 40:574–581 (1985); and Cosgrove et al., Journal of Thoracic Cardiovascular Surgery 88:673–684 (1984). Aortic atheroma increases sharply with age, from 20% in the fifth decade at necropsy to 80% over the age of 75 years, and stroke rate increases from 1% in patients 51 to 60 years to 7% or more in those over 75 years. See Fisher et al., Journal of Neuropathology and Experimental Neurology 24:455–476 (1965); Amarenco et al., Stroke 23:1005–1009 (1992); Marschall et al., Journal of Cardiothoracic Vascular Anesthesia 8:5–13 (1994); Blauth et al., Journal of Thoracic Cardiovascular Surgery 103:1104–1112 (1992); Wareing et al., Annals of Thoracic Surgery 55:1400–1408 (1993); and Davila-Roman et al., Circulation 84 III-47-III-53, 1991 [suppl 3]; Wareing et al., Journal of Thoracic Cardiovascular Surgery 103:453–462 (1992); Gardner et al., Annals of Thoracic Surgery 40:574–581 (1985); Cosgrove et al., Journal of Thoracic Cardiovascular Surgery 88:673–684 (1984); Davila-Roman et al., Stroke 25:2010–2016 (1994); Bar-El et al., Journal of Thoracic Cardiovascular Surgery 104:469–474 (1992); and Saloman et al., Journal of Thoracic Cardiovascular Surgery 101:209–218 (1991). Among patients dying after coronary bypass surgery, evidence of atheroembolism was present in only 4.5% in 1982, and in as many as 48% in 1989. See Wareing et al., Journal of Thoracic Cardiovascular Surgery 103:453–462 (1992).

Embolization from the aorta, particularly to the brain, is therefore a major problem, and emboli from this source can lead to stroke, myocardial infarction, kidney infarcts, and peripheral emboli in other organs. There is a presently unfulfilled need for an atherectomy device for use in the aorta to prevent the above identified disorders arising from embolization. Moreover, it will be understood that fixed plaque exists both in the aorta and in the carotid arteries which may also lead to stroke by embolization. Thus, there is a presently unfulfilled need for an atherectomy device for use in both aorta and carotid arteries to prevent embolization from such fixed plaque. Another site at which fixed plaque may build up is in the iliac and femoral arteries. Claudication may result from inadequate blood flow in or embolization to the iliac and femoral arteries. A need therefore exists for an atherectomy device for use in the iliac and femoral arteries to prevent claudication by increasing blood flow and also preventing embolization to the lower extremities.

The coronary arteries, by contrast, present entirely different considerations with respect to atherectomy. In the coronary arteries, myocardial ischemia or infarction is typically caused by a reduction in blood flow by reason of the build up of atheroma causing stenosis, rather than dislodgement of embolic material from such plaques. Atherectomy in the coronary arteries therefore prevents myocardial infarction by increasing blood flow due to an enlargement of the luminal diameter on removal of stenosis. Accordingly, there exists an extensive body of literature which addresses the use of atherectomy in relation to stenosis as applied in the coronary arteries. For example, Fischell, U.S. Pat. No. 5,409,454, discloses a retrograde cutting atherectomy catheter designed to perform atherectomy on an eccentric stenosis by cutting plaque from one part of an arterial wall while shielding a normal portion of the arterial wall from being cut. Fischell, U.S. Pat. No. 4,898,575, discloses a tunneling catheter system which rides on a guidewire for percutaneous transluminal atherectomy. Rydell, U.S. Pat. No. 4,857,045, discloses an atherectomy catheter having a motor driven cutting member and capabilities for flushing the treatment site and aspirating a flushing liquid so as to remove debris loosened during a procedure. Moreover, Yock, U.S. Pat. Nos. 4,794,931, 5,000,185, and 5,313,949, disclose catheters having a cutting member for atherectomy and an ultrasound transducer which enables ultrasonography in combination with atherectomy. Meanwhile, Jang et al., U.S. Pat. No. 5,507,292, discusses abrasive atherectomy in combination with ultrasound imaging. The patent and medical literature is replete with additional disclosures of atherectomy as applied to the coronary arteries, and this subject will not be further discussed here for the sake of brevity. The interested reader is referred to the following disclosures for more information: Farr, U.S. Pat. Nos. 4,950,277, 4,986,807, 5,019,088, Shiber, U.S. Pat. Nos. 4,894,051, 4,957,482, 4,979,939, 5,007,896, 5,024,651, 5,135,531, Summers, U.S. Pat. No. 5,087,265, Plassche et al., U.S. Pat. No. 5,318,576, Belknap, U.S. Pat. No. 5,366,464, Jang et al., U.S. Pat. No. 5,402,790, Mazur et al., Catherization and Cardiovascular Diagnosis 31:79–84 (1994), Fischell et al., U.S. Pat. Nos. 4,886,061, 5,100,425. It will be appreciated that coronary artery atherectomy devices do not prevent embolization, but this does not appear to be a major consequence during this procedure.

Insofar as we are aware, however, there has been no disclosure of an atherectomy catheter adapted for trapping and removing mobile plaque or fixed plaque in the aorta, carotid, or femoral arteries and having an ability to remove embolic material generated during the procedure. Accordingly, a need exists for an arterial atherectomy catheter having an ability to entrap and/or snare, and thereafter remove aortic, carotid, and femoral artery plaque without generating atheromatous embolization.

SUMMARY OF THE INVENTION

We have discovered that mobile aortic plaque present in the aorta is a major contributor to the occurrence and recurrence of ischemic stroke. Mobile aortic plaque is a term that refers to vascular deposits comprising a solidified base and a floppy projection attached to the base. The floppy projection is most easily dislodged by normal pulsating blood flow or by an invasive procedure such as angiography, angioplasty, stenting, or cardiac surgery, and may produce embolic material. The build up of mobile aortic plaque, as well as the number and extent of the floppy projections, increases with age and therefore the risk of ischemic stroke, myocardial infarction, and systemic emboli due to release of a floppy projection into the blood stream also increases with age.

Atherectomy of the aorta can prevent each of the above diseases from occurring, but can also cause these diseases unless the atherectomy device is specially designed to enter the aorta without scraping against plaque, or includes a filter which is inserted and deployed to capture embolic material dislodged during the procedure. While reduction in blood flow is typically not a problem in the aorta due to the large diameter of this vessel, in the carotid arteries, fixed plaque poses a risk of stroke by embolization, and presents an additional threat of reducing blood flow by occluding the vessel lumen. Thus, atherectomy in the carotid arteries can prevent stroke by either increasing blood flow or reducing the potential for formation of embolic material. However, carotid atherectomy also poses a risk in that the atherectomy instrument can dislodge plaque, and thereby cause stroke by embolization. Fixed plaque is also present in the descending aorta and its dislodgement may cause kidney infarcts or ischemia to other end-organs. Fixed plaque is also present in the iliac arteries and femoral arteries which in turn may cause peripheral leg ischemia either through distal embolization of atheromatous material or through in situ stenosis of the diseased blood vessel (narrowing of luminal diameter). Femoral artery atherectomy prevents appendicular claudication caused by plaque occluding the lumen of the femoral artery; atherectomy, however, results in distal embolization of atheromatous material which in turn may cause limb ischemia.

The present invention relates to arterial medical devices which are adapted to remove mobile aortic plaque without generating embolic material which can create a risk of ischemic stroke. As discussed above, numerous medical devices have been proposed for atherectomy in the coronary arteries. However, these devices do not reduce the risk of embolization associated with such procedures; the catheters themselves are likely to dislodge plaque material during positioning, and these devices do not include structures to prevent escape of embolic material. By contrast, the devices of the present invention generally include an arterial atherectomy catheter having suction means or a mechanical trapping device which acts to draw in and secure a mobile plaque. Mobile plaque, without trapping, presents a target difficult to maintain in contact. The atherectomy devices herein further include a cutting member to excise plaque once captured by the device, and optionally include a blood filter mechanism. Moreover, the invention includes methods of using the devices to remove plaque from the aortic wall, aortic valve, carotid arteries, and/or femoral artery. Those devices which include a filter mechanism will remove embolic material from blood, and thereby prevent occurrence of ischemic stroke, myocardial infarction or systemic embolus. Embolic material in this setting is any constituent of blood, or atheromatous material and superimposed thrombus, which may cause complications in the body if allowed to travel freely in the blood stream. This matter includes, but is not limited to, atheromatous fragments, fat, platelets, fibrin, clots, or gaseous material.

In one embodiment, the medical device comprises an arterial catheter system which includes a flexible elongate member or catheter having an outer surface, a distal region adapted to enter an artery, and a proximal region which extends from a patient's vessel and permits control outside the patient's body by a physician. At the distal region of the catheter is provided an atherectomy assembly which includes an excising member, e.g., a cutting blade, abrasive member, wire cutter, jaws, claws, pincher, snare, etc., and a trapping mechanism which, in certain embodiments, comprises an open-ended tubular member which extends to the proximal region of the catheter and is attached to a vacuum source. In other embodiments, the trapping mechanism comprises a snare, adjustable orifice, basket, grabber, opening in a tube, etc. The trapping and cutting of plaque may occur simultaneously or sequentially in either order. The atherectomy assembly may optionally further include means for intravascular imaging, e.g., an ultrasonic transducer, which means are fully described in the art and will not be further discussed here.

The arterial catheter system may also include a filtration mesh, typically disposed circumferentially about the distal region of the catheter. Devices for use in the aorta and femoral artery will typically have the filtration mesh proximal to the atherectomy assembly, whereas the catheter for carotid artery atherectomy will have the filtration mesh distal to the atherectomy assembly, so that in all cases filtration occurs downstream of atherectomy. The filter will typically include a continuous mesh having a first edge which is closely associated with the outer surface of the catheter and a second edge attached to an expansion mechanism which is expandable between a contracted condition and an enlarged condition. The construction and use of expansion means and associated filter mesh on an arterial blood cannula have been thoroughly discussed in our earlier applications including Barbut et al., U.S. application Ser. No. 08/553,137, filed Nov. 7, 1995, Barbut et al., U.S. application Ser. No. 08/580,223, filed Dec. 28, 1995, Barbut et al., U.S. application Ser. No. 08/584,759, filed Jan. 9, 1996, Barbut et al., U.S. application Ser. No. 08/640,015, filed Apr. 30, 1996, and Barbut et al., U.S. application Ser. No. 08/645,762, filed May 14, 1996, and the contents of each of these prior applications are incorporated herein by reference in their entirety. It will be understood that the design and use of a filter mesh and associated expansion means as discussed in these applications is fully applicable to the use of such filter and expansion means on an arterial catheter system as disclosed herein. Moreover, it will be understood that the filter mesh need not be disposed circumferentially about the catheter, but may be arranged on one side, or distal to the distal end of the catheter. These other configurations are possible so long as the filter may be expanded to cover substantially the entire vessel lumen so that substantially all blood flowing downstream is filtered.

The methods of the present invention include protecting a patient from embolization during an atherectomy procedure to remove plaque from the aorta (aortic wall, aortic valve, or aortic root), common carotid artery, external and internal carotid arteries, brachiocephalic trunk, middle cerebral artery, anterior cerebral artery, posterior cerebral artery, vertebral artery, basilar artery, subclavian artery, brachial artery, axillary artery, iliac artery, renal artery, femoral artery, popliteal artery, celiac artery, superior mesenteric artery, inferior mesenteric artery, anterior tibial artery, posterior tibial artery and all other arteries carry oxygenated blood. The physician will typically determine the presence and location of mobile plaque using one or more of a number of visualization techniques including transesophageal echocardiography (TEE), epiaortic ultrasonography. Another visualization technique, intravascular ultrasound, may also be useful in evaluating the presence and location of mobile plaque in the aorta, carotid, and femoral artery. Unlike the other techniques mentioned, intravascular ultrasound visualizes the blood vessel from its inside. Transcranial Doppler ultrasonography may be used for cerebral monitoring of emboli during the atherectomy procedure.

In use, the distal end of the arterial catheter is inserted and deployed through an incision in the femoral or brachial artery in a manner widely used for deployment of coronary artery angioplasty, atherectomy, and ultrasonography catheters. Thus, certain procedures are so-called de novo catheterizations performed for the purpose of removing plaque from the aorta, common carotid artery, external and internal carotid arteries, brachiocephalic trunk, middle cerebral artery, anterior cerebral artery, posterior cerebral artery, vertebral artery, basilar artery, subclavian artery, brachial artery, axillary artery, iliac artery, renal artery, femoral artery, popliteal artery, celiac artery, superior mesenteric artery, inferior mesenteric artery, anterior tibial artery, posterior tibial artery and all other arteries carry oxygenated blood. In other cases, the present invention will be an add-on procedure at the end of, or possibly before, a cardiac catheterization procedure. In either case, the procedure will typically be conducted in a standard "catheterization laboratory" rather than an operating room, although use in an operating room is an option.

The distal region of the catheter is advanced within the femoral or brachial artery until the distal end reaches a region of interest in the aorta, carotid, or femoral artery (a region having plaque which is to be removed). Advancement of the catheter tip may be assisted by X-ray fluoroscopy, and the distal region of the catheter may include one or more fluoroscopic markers to enable such visualization. Advancement may also be assisted by IVUS or TEE, or by a conventional guidewire and/or a guiding catheter, both of which are known in the art for coronary catheterization. Typically, it is difficult to navigate the aortic arch without some assistance from visualization, mechanical guidance, or both. Where associated filtration is to be used (a feature which is optional), the expansion means, including associated mesh, is inflated or deployed to expand and thereby achieve contact if need be with the inner wall of the artery. Once the filtration means are in place and deployed, a trapping mechanism (suction, claws, jaws, or an orifice with a mouth having an adjustable opening) is positioned in close proximity to the plaque of interest, and thereafter activated in order to draw in and secure the plaque. In the absence of such a grabbing mechanism, the plaque would present a moving target which is difficult to cut with any degree of accuracy, and could embolize by reason of contact with the medical device.

The plaque is securely held by the atherectomy assembly, and a cutting mechanism is deployed to remove or excise the plaque or a portion thereof. For atherectomy of mobile aortic plaque, it will be understood that before, during and after cutting, the floppy projection is typically held secure by the atherectomy assembly and therefore does not itself present a risk of release to form an embolus. In certain embodiments, grabbing and cutting of plaque will be simultaneously conducted, while in other embodiments, these steps are sequential and in either order. However, it is desirable to have an associated filter deployed downstream of the atherectomy assembly because the process of immobilizing and cutting plaque material may cause dislodgement of embolic material from the region of interest in the artery.

After the mobile plaque is excised and retained in the atherectomy device, the expansion means and filtration system, if used, are contracted by deflating or collapsing to resume a small shape in close contact with the outer surface of the catheter. The catheter, with captured embolic material in the atherectomy and optionally in the filtration system, is then withdrawn from the artery of interest and back into the femoral artery where it is ultimately removed from the patient's body.

BRIEF DESCRIPTION OF DRAWINGS

Reference is now made to a brief description of the drawings, which are intended to illustrate an arterial catheter system for use herein. The drawings and detailed description which follow are intended to be merely illustrative and are not intended to limit the scope of the invention as set forth in the appended claims.

FIG. 9A depicts an atherectomy assembly in accordance with another embodiment having a basket with an adjustable opening at a distal end;

FIG. 9B depicts the atherectomy assembly of FIG. 9A in a collapsed condition;

FIG. 10 depicts an atherectomy cutting assembly having a adjustable orifice for trapping plaque and a cutting blade operably disposed beneath the adjustable orifice;

FIG. 15A shows an atherectomy assembly in an alternative embodiment, having forward grabbing capabilities, while

FIGS. 16A and 16B show an atherectomy assembly in an alternative embodiment, viewed from a side and from above;

FIG. 16C shows the atherectomy assembly of FIG. 16A as viewed from its distal end, while FIG. 16D shows the atherectomy assembly of FIG. 16C in a closed configuration;

DETAILED DESCRIPTION

Figure 1:
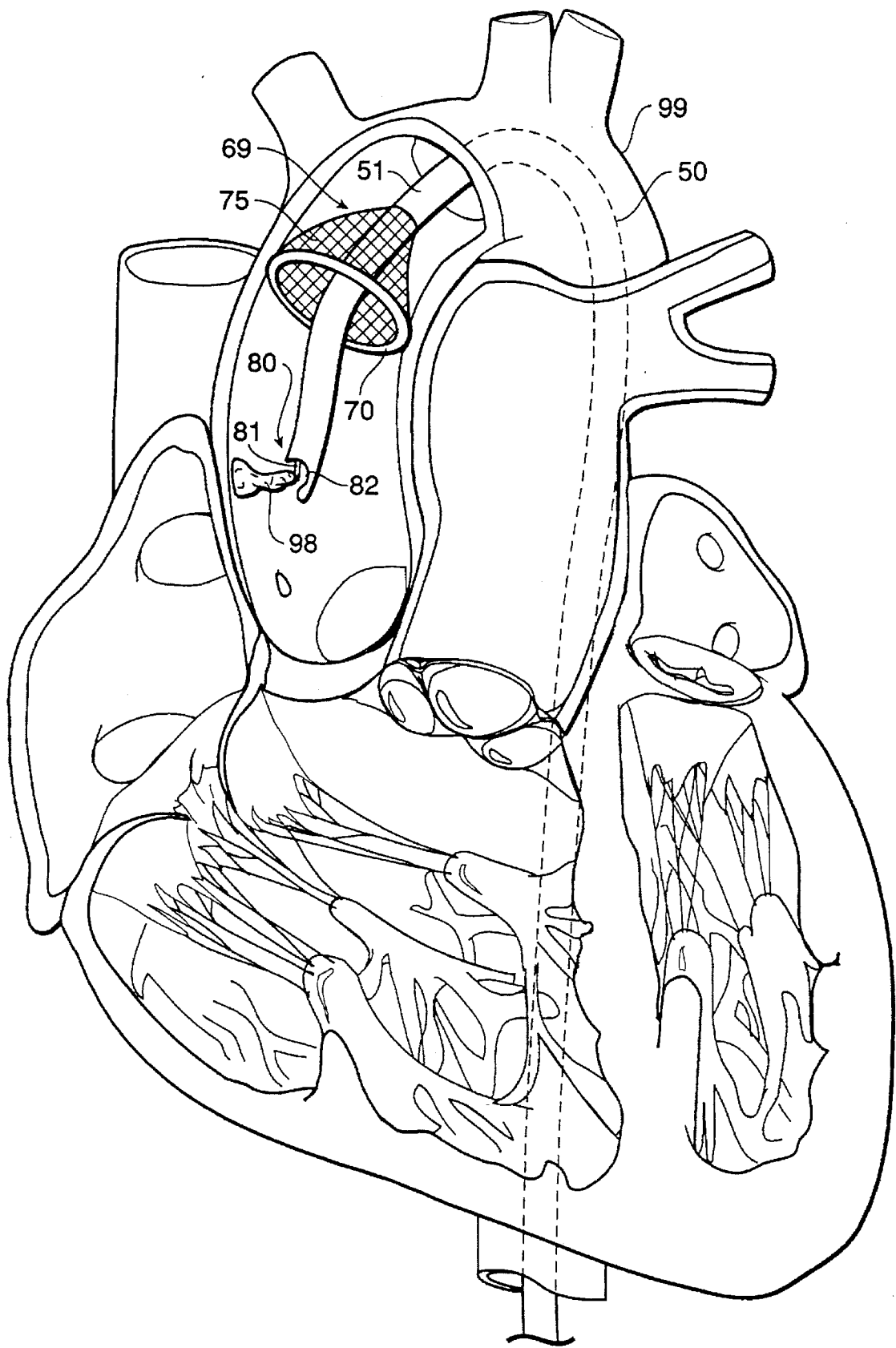
FIG. 1 is a longitudinal view of an arterial catheter system having its distal end positioned in the ascending aorta during use.

In a first embodiment, an arterial atherectomy catheter with associated filter is provided as depicted in FIG. 1. The catheter system includes a flexible elongate member 50 having an outer surface, a distal region 51 adapted to enter an artery, and a proximal region. In certain embodiments, the catheter system includes filtration assembly 69 having an expansion means, typically comprising inflation seal 70, disposed about distal region 51 of flexible elongate member 50, wherein inflation seal 70 is expandable between a contracted condition and an enlarged condition. The filtration assembly will further include mesh 75 which is operably connected to inflation seal 70 at a first edge, and is closely associated with the outer surface of elongate member 50 at a second edge. Thus, in a contracted condition, inflation seal 70 and mesh 75 can be inserted through the femoral artery and up through aorta 99 into a region of interest, and thereafter expanded by injection of fluid or gas into inflation seal 70 to thereby achieve contact with the inner lumen of aorta 99. The arterial catheter system further includes atherectomy assembly 80 disposed within distal region 51 of elongate member 50, and distal to filtration assembly 69. Atherectomy assembly 80 generally includes cutting blade 81 or other means to remove atheromatous plaque from aorta 99 or the femoral artery, and suction means 82 which may comprise the inner lumen of catheter 50, or a separate tubular member carried therein. During operation, mobile aortic plaque 98 is trapped and held securely by suction means 82 and simultaneously excised from the arterial lumen by cutting blade 81.

Figure 2:
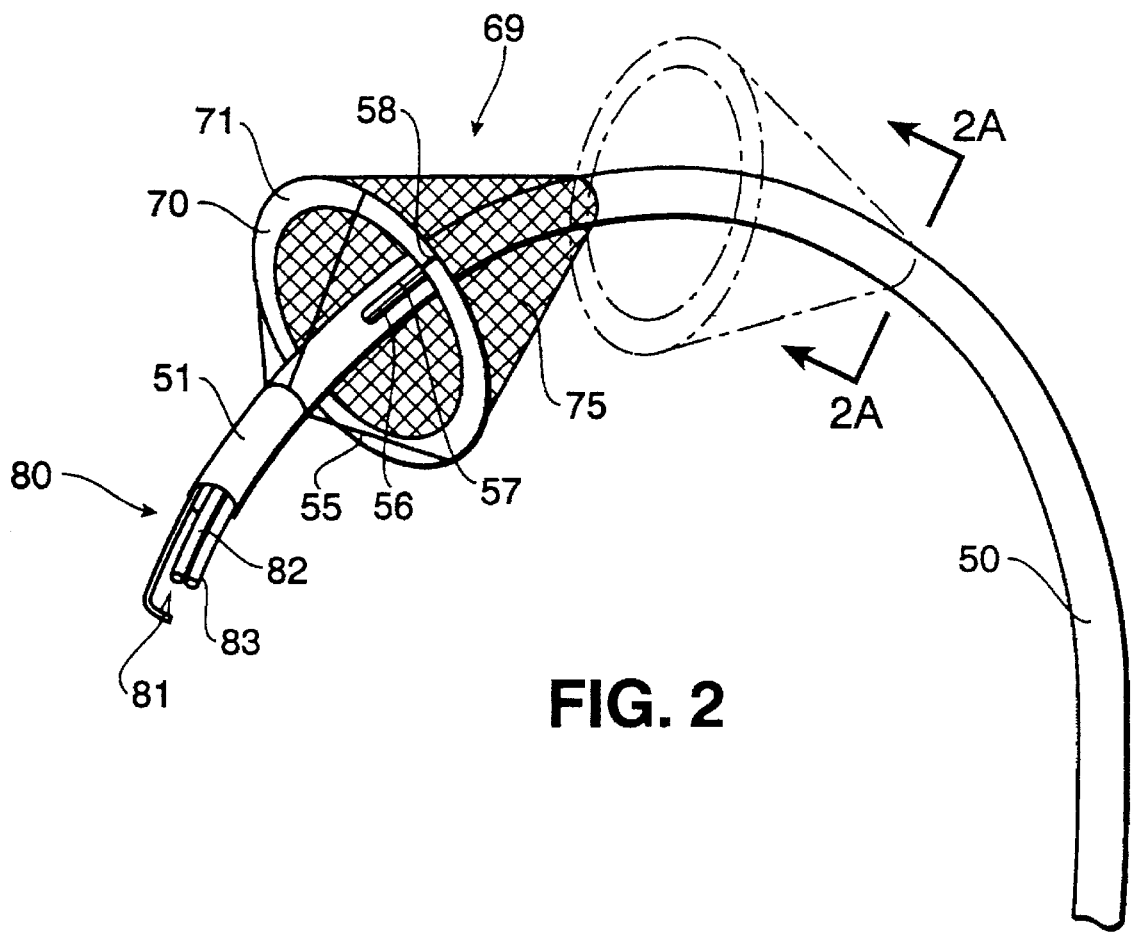
FIG. 2 is a longitudinal view of an arterial catheter system for use as depicted in FIG. 1, shown without a surrounding vessel.

An exploded view of the arterial catheter system is depicted in FIG. 2. For this embodiment, elongate member 50 includes atherectomy assembly 80 at its distal end. The atherectomy assembly includes distally located cutting blade 81, suction means 82 comprising a separate tubular member housed within the lumen of elongate member 50 and which may or may not extend beyond the distal opening of elongate member 50, and means for intravascular imaging 83 which may include an ultrasound transducer for intravascular ultrasound which is constructed in accordance with technology well known in the art. Where IVUS is used, the IVUS component may be deployed through a separate or the same catheter which houses the atherectomy assembly.

In certain embodiments as discussed above, filtration is an important feature of the atherectomy catheter. To filter blood effectively, i.e., to capture embolic material, without unduly disrupting blood flow, the mesh must have the appropriate physical characteristics, including area ($A_M$), thread diameter ($D_T$), and pore size ($S_P$). In the aorta, the mesh 75 must permit flow rates as high as 3 L/min or more, more preferably 3.5 L/min or more, more preferably 4 L/min or more, more preferably 4.5 L/min or more, more preferably 5 L/min or more preferably 5.5 L/min or more, and most preferably 6 L/min or more at pre-filter maximum systolic pressures (proximal to the mesh) of around 200 mm Hg or less.

The plaques to be excised by the atherectomy procedures herein will vary in size, and may be as large as 2 cm in diameter, more typically 1.5 cm or larger in diameter, more typically 1 cm or larger in diameter, more typically 0.5 cm or larger in diameter, more typically 0.1 cm or larger in diameter. The particles of plaque inadvertently dislodged during a procedure are generally much smaller, and these dislodged particles are the particles to be captured by the filtration system. In order to capture as many dislodged particles as possible, mesh with the appropriate pore size must be chosen. With reference to embolic material dislodged from the aorta, individual particle diameter ranges from 0.05 mm to 2.88 mm, with a mean diameter of 0.85 mm, and individual particle volume ranges from $6.5 \times 10^{-5}$ mm$^3$ to 12.45 mm$^3$, with a mean particle volume of 0.32 mm$^3$. Approximately 27 percent of the particles have been found to measure 0.6 mm or less in diameter. During cardiac bypass surgery in particular, the total aortic embolic load has been found to range from 570 mm$^3$ to 11200 mm$^3$, with a mean of 3700 mm$^3$, and an estimated cerebral embolic load has been found to range from 60 mm$^3$ to 510 mm$^3$, with a mean of 276 mm$^3$. During aortic atherectomy, materials dislodged as emboli have similar characteristics.

By way of example, when a device as disclosed herein is intended for use in the aorta, the area of the mesh required for the device is calculated from Bernoulli's equation as described in our earlier applications including Barbut et al., U.S. application Ser. No., U.S. application Ser. No. 08/553,137, filed Nov. 7, 1995, Barbut et al., U.S. application Ser. No. 08/580,223, filed Dec. 28, 1995, Barbut et al., U.S. application Ser. No. 08/584,759, filed Jan. 9, 1996, Barbut et al., U.S. application Ser. No. 08/640,015, filed Apr. 30, 1996, and Barbut et al., and U.S. application Ser. No. 08/645,762, filed May 14, 1996.

In an embodiment of an arterial atherectomy catheter that is to be used in the aorta, mesh with dimensions within the following ranges is desirable: mesh area is 0.5–10 in$^2$, more preferably 1–9 in$^2$, more preferably 2–8 in$^2$, more preferably 3–8 in$^2$, more preferably 4–8 in$^2$, more preferably 5–7 in$^2$; mesh thickness is 60–280 µm, more preferably 70–270 µm, more preferably 80–260 µm, more preferably 90–250 µm, more preferably 100–250 µm, more preferably 120–230 µm, more preferably 140–210 µm; thread diameter is 30–145 µm, more preferably 40–135 µm, more preferably 50–125 µm, more preferably 60–115 µm, more preferably 70–105 µm, and pore size is 500 µm or less, more preferably 400 µm or less, more preferably 300 µm or less, more preferably 200 µm or less, more preferably 100 µm or less, more preferably 50 µm or less and usually larger than at least a red blood cell. In a preferred embodiment of the invention, mesh area is 2–8 in$^2$, mesh thickness is 60–200 µm, thread diameter is 30–100 µm, and pore size is 50–300 µm. In a further preferred embodiment of the invention, mesh area is 3–5 in$^2$, mesh thickness is 60–150 µm, thread diameter is 50–80 µm, and pore size is 100–250 µm.

Once appropriate physical characteristics are determined, suitable mesh can be found among standard meshes known in the art. For example, polyester meshes may be used, such as meshes made by Saati Corporations and Tetko Inc. These are available in sheet form and can be easily cut and formed into a desired shape. In a preferred embodiment, the mesh is sonic welded into a cone shape. Other meshes known in the art, which have the desired physical characteristics, are also suitable. Anticoagulants, such as heparin and heparinoids, may be applied to the mesh to reduce the chances of blood clotting on the mesh. Anticoagulants other than heparinoids also may be used, e.g., monoclonal antibodies such as ReoPro (Centocor). The anticoagulant may be painted or sprayed onto the mesh. A chemical dip comprising the anticoagulant also may be used. Other methods known in the art for applying chemicals to mesh may be used.

In an embodiment of the devices suited for placement in the aorta, the expansion means, upon deployment, has an outer diameter of approximately 20 mm, more preferably 25 mm, more preferably 30 mm, more preferably 35 mm, more preferably 40 mm, and most preferably 42 mm, or greater. The expansion means, when fully inflated, has a thickness of 2–5 mm. The dimensions of the expansion means may be adjusted in alternative embodiments adapted for use in vessels other than the aorta. Alternatively, expandable members other than a balloon also may be used with this invention. Other expandable members include the umbrella frame with a plurality of arms as described in U.S. application Ser. Nos. 08/533,137, 08/580,223, and 08/584,759.

All components of this device should be composed of materials suitable for insertion into the body. Additionally, sizes of all components are determined by dimensional parameters of the vessels in which the devices are intended to be used. These parameters are known by those skilled in the art.

Filtration of blood in the aorta will usually be conducted while the heart is functioning normally, i.e., without the use of cardiopulmonary bypass. Thus, blood pressure will be typically 50–200 mm Hg, blood flow will be approximately 5 L/min., and the pressure gradient will have no more than a 40 mm Hg drop across the filter when open (i.e., the filter may not be used in some embodiments). Modification of the operational characteristics set forth above for use in vessels other than the aorta are readily ascertainable by those skilled in the art in view of the present disclosure. An advantage of all embodiments including a filter disclosed herein is that the blood filter will capture emboli which may result from the atherectomy procedure which is performed using the distal end of the catheter. Another advantage is that both the atherectomy assembly and the filter means enter the vessel through the same incision created for the catheter, and therefore the devices and methods herein economize on incisions made in the blood vessel, often the femoral artery.

In addition, use of visualization techniques is also contemplated in order to determine the location and size of mobile aortic plaque, and to help position the atherectomy assembly to engage mobile plaque which is to be excised. In particular, it is desirable to have a catheter having steering capabilities so that the tip can be guided to position the atherectomy assembly to engage plaque. Steerability can be accomplished using pull wires in accordance with techniques known in the art. See Edwards et al., U.S. Pat. No. 5,409,453, Lundquist et al., U.S. Pat. Nos. 5,395,327, 5,254,089, 5,336,182, 5,254,088, 5,315,996, 5,254,088, 5,195,968, and 5,531,686, Jaraczewski et al., U.S. Pat. Nos. 5,487,757 and 5,318,525, and Truckai, U.S. Pat. No. 5,397,304. Steering capabilities may permit single axis steering (bending in a plane), or double axis steering (bending in 3-dimensional space), such as is known in the art for electrophysiology catheters. The range of motion for the catheter tip should permit bending (from a straight catheter) to 30°, more preferably to 60°, more preferably to 90°, more preferably to 120° or more. In a preferred embodiment, steering is used in conjunction with TEE or intravascular ultrasound to locate and position the catheter tip near to a plaque, and engage the plaque. Moreover, visualization techniques can be used to determine which patients require filtration (identify risk factors), where to effectively position a blood filter device to maximize effectiveness, when to adjust the device if adjustment is necessary, when to actuate the device, and appropriate regions for performing any procedures required on a patient's blood vessel.

In accordance with one aspect of the invention, a visualization technique, such as TEE or intravascular ultrasound, is used to assist with placement of the atherectomy assembly, and to determine when to actuate a blood filter device. For example, during aortic atherectomy, emboli may be dislodged during positioning of the atherectomy assembly, as well as during operation of the cutting assembly. Therefore, a mesh may be opened within a vessel downstream of the aorta during these procedures and closed when embolization resulting from these procedures has ceased. Closing the mesh when filtration is not required helps to minimize obstruction of the blood flow and minimize the dislodgement of emboli by the filter itself.

According to another embodiment, a visualization technique is used to locate a series of mobile plaques in the aorta. The catheter may then be operated iteratively to locate by TEE, IVUS, or other imaging technique and remove each plaque from the descending aorta to the aortic root, and even on the aortic valve. It will be understood that, where iterative atherectomy is performed, the atherectomy assembly and/or catheter should have an ability to store excised plaque on board without having it escape into the blood stream. Thus, the catheter may be equipped with apparatus to grind, abrade, or break plaque into smaller particles for storage or aspiration through a lumen of the catheter. In one embodiment, a cutter blade will advance and remove plaque and deposit the plaque in a distal cavity within a housing. In another embodiment, the excised plaque is drawn away from the site of cutting by suction. The plaque may be drawn proximally by aspiration until it reaches an area where it can be stored, usually a short distance proximal within the housing. In another embodiment, plaque is abraded by an abrasive member and aspirated or otherwise stored in the catheter housing. In yet a further embodiment, the catheter provides an auger which is used to bore through a plaque. The tool may have a substantially helical blade which, when rotated, advances excised particles proximally, as if caught in the threads of a rotating screw.

Visualization can also be used to follow the progress of the atherectomy procedure, and to monitor emboli in the aorta to evaluate the effectiveness of a blood filter device in trapping emboli. Moreover, the user can engage and excise additional plaque if monitoring indicates that a first cutting procedure has not adequately removed the portion of plaque presenting a risk to a patient, or if the first cutting procedure reveals a second plaque material buried under a first plaque which has already been removed. According to yet another embodiment, a visualization technique, such as intravascular ultrasonography, TEE, and epicardial aortic ultrasonography, is used as described above, and to identify those patients requiring blood filtration according to the present invention. For example, these visualization techniques may be used to identify patients who are likely to experience embolization due to the presence of mobile plaque. These techniques may be used before the patient undergoes any type of procedure which will affect a blood vessel in which mobile plaque is located. Transcranial Doppler may be used for cerebral monitoring of emboli during the atherectomy procedure.

Visualization techniques, other than those already mentioned, as are known to those skilled in the art, are also useful in ascertaining the contours of a blood vessel affected by surgical procedure to assess a variety of risk factors for embolization, and to locate appropriate sections of a vessel for performing certain procedures. Any suitable visualization device may be used to evaluate the efficacy of a device, such as those disclosed herein, in trapping emboli.

With reference to FIG. 1, the distal region of flexible elongate member 50 is shown with blood filtration means deployed in the ascending region of a human aorta 99.

Flexible catheter 50 will typically be of a size no greater than about 10 F, and this size is dictated by the size of the introducer used in the femoral artery. Catheter size is not generally restricted by the vessel lumen because the aorta has an internal lumen of about 10–40 mm. The distal region of flexible elongate member 50 is shown again in FIG. 2, and may include a plurality of spokes or holding strings 55 made from Dacron® or other suitable material. Holding strings 55 connect distal region 51 of catheter 50 to expansion means 70, preferably an inflation seal which comprises a continuous ring of thin tubing attached to filter mesh 75 on its outer edge. Alternative expansion means based on a mechanical expanding mechanism similar to an umbrella frame are described in U.S. application Ser. Nos. 08/553,137, 08/580, 223, 08/584,759, 08/640,015, and 08/645,762. Filter mesh 75 is bonded at a second edge around the circumference of the outer surface of catheter 50, preferably at a cross-sectional position near distal end 51 of catheter 50.

Inflation seal 70 may be constructed from elastomeric or non-elastomeric tubular material which encloses a donut-shaped chamber 71. When deployed, the inflation seal will expand to a diameter which fits tightly against the lumen of aorta 99 or femoral artery. The inflation seal will thus be capable of expansion to an outer diameter of at least 1 cm, more preferably at least 1.5 cm, more preferably at least 2 cm, more preferably at least 2.5 cm, more preferably at least 3 cm, more preferably at least 3.5 cm, more preferably at least 4 cm, more preferably at least 4.5 cm, more preferably at least 5 cm, more preferably at least 5.5 cm, more preferably at least 6 cm. These ranges cover suitable diameters for both pediatric use and adult use. The inflation seal is typically a continuous ring of very thin tubing attached on one side to the filter mesh and on the other side to the pressurizing cannula by holding strings.

The inflation seal should be able to maintain an internal pressure in chamber 71, without bursting, of greater than 55 mm Hg, more preferably greater than 60 mm Hg, more preferably greater than 70 mm Hg, more preferably greater than 80 mm Hg, more preferably greater than 90 mm Hg, more preferably greater than 100 mm Hg, more preferably greater than 110 mm Hg, more preferably greater than 120 mm Hg, more preferably greater than 130 mm Hg, more preferably greater than 140 mm Hg, more preferably greater than 150 mm Hg. The internal pressure needed will depend on the pressure maintained in the aorta against the mesh. Thus, if the aortic pressure is 55 mm Hg, then the pressure in the inflation seal must be greater than 55 mm Hg to prevent leakage around the seal. Typically, the aortic pressure will be at least 75 mm Hg because this level of pressure is needed to ensure adequate brain perfusion. It will be recognized that such inflation seal pressures are much higher than the maximum level that can be used in the pulmonary venous system because the veins and arteries therein will typically hold no more than about 40–50 mm Hg, or at most 60 mm Hg without rupture.

Figure 2A:
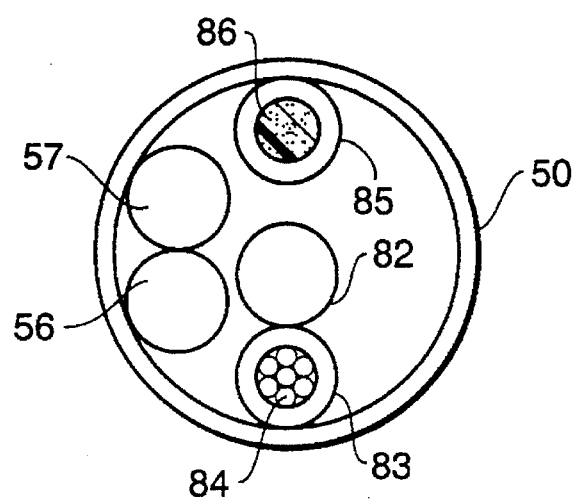
FIG. 2A is a cross-sectional view of the catheter depicted in FIG. 2 shown through section line 2A—2A.

Chamber 71 is in fluid communication with first tubular passage 56 and second tubular passage 57 which permit chamber 71 to be inflated with gas, or preferably a fluid such as saline. The first tubular passage 56 is in fluid communication with lumen 56 (shown in FIG. 2A) of flexible elongate member 50, while second tubular passage 57 is in fluid communication with lumen 57 of pressurizing cannula 50. The first and second tubular passages thereby interconnect chamber 71 with the inflation and evacuation lumens, respectively, of flexible elongate member 50.

In certain embodiments, inflation seal 70 will include septum 58 which blocks the movement of fluid in one direction around chamber 71. If the septum is positioned in close proximity to the fluid entry port, then the injection of fluid will push all gas in chamber 71 around inflation seal 70 and out through the second passage. In one embodiment, the entry port and the exit port are positioned in close proximity, with the septum disposed between the entry and exit port. In this case, injection of fluid will force virtually all gas out of inflation seal 70.

Filter mesh 75 is bonded at a first edge to inflation seal 70 and at a second edge to flexible elongate member 50. Mesh 75 can be made of a material which is reinforced or non-reinforced. Mesh 75, when expanded as shown in FIGS. 1 and 2, may assume a substantially conical shape with a truncated distal region. The mesh should be formed of a material having a pore size which captures objects 5 mm in diameter or less, more preferably 3 mm in diameter, more preferably less than 3 mm, more preferably less than 2.75 mm, more preferably less than 2.5 mm, more preferably less than 2.25 mm, more preferably less than 2 mm, more preferably less than 1.5 mm, more preferably less than 1 mm, more preferably less than 0.75 mm, more preferably less than 0.5 mm, more preferably less than 0.25 mm, more preferably less than 0.1 mm, more preferably less than 0.075 mm, more preferably less than 0.05 mm, more preferably less than 0.025 mm, more preferably 0.02 mm, and down to sizes just larger than a red blood cell. It will be understood that for a given pore size that blocks particles of a certain size as stated above, that pore size will block all particles larger than that size as well. It should also be understood that the necessary pore size is a function of blood throughput, surface area of the mesh, and the pressure on the proximal and distal side of the mesh. For example, if a throughput of 5–6 L/min. is desired at a cross-section of the aorta having a diameter of 40 mm, and a pressure of 120 mm Hg will be applied to the proximal side of the mesh to obtain a distal pressure of 80 mm Hg, then a pore size of about $\geq 50$ μm is needed. By contrast, in the pulmonary artery the same throughput is needed, but the artery cross-section has a diameter of only 30 mm. Moreover, the proximal pressure is typically 40–60 mm Hg, while the distal pressure is about 20 mm Hg. Thus, a much larger pore size is needed to maintain blood flow. If pore sizes as disclosed herein for the aorta were used in the pulmonary artery, the blood throughput would be insufficient to maintain blood oxygenation, and the patient would suffer right ventricular failure because of pulmonary artery hypertension. If pore sizes as used in the pulmonary artery were used in the aorta or femoral artery, adequate blood oxygenation would be maintained, but a flurry of embolic material would escape filtration because the pore sizes of the mesh are too large to capture smaller size embolic materials.

Figure 3:
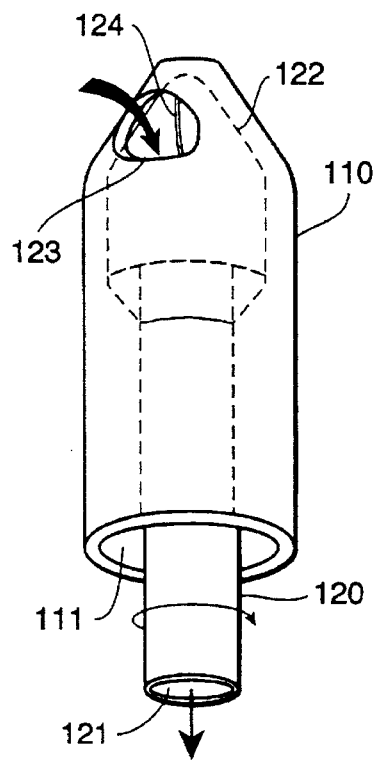
FIG. 3 depicts an atherectomy cutting assembly for use in an arterial catheter system as disclosed herein.
Figure 5:
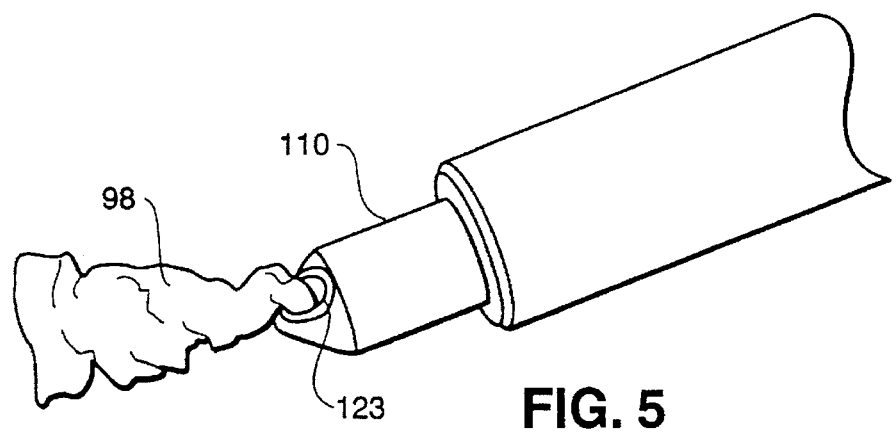
FIG. 5 depicts an atherectomy cutting assembly as shown in FIG. 3 having a mobile aortic plaque engaged by the cutting assembly.

With reference to FIG. 2, it will be understood that cutting means 81 and suction means 82 may be replaced by any of a number of atherectomy working elements which allow trapping of mobile aortic plaque by suction and simultaneous removal of at least a portion of this plaque by curing. Thus, one embodiment of an atherectomy curing device is depicted in FIG. 3. The curing assembly includes housing 110 which may be formed integral with or molded onto the distal tip of flexible elongate member 50. The distal region of housing 110 includes opening 123 shaped to receive a portion, including the floppy region, of mobile aortic plaque. A flexible rotatable member 120 is disposed within lumen 111 of housing 110 and is shaped to permit rotation as well as longitudinal translation relative to housing 110. Rotatable member 120 has an interior lumen 121 which extends proximal from the distal region of rotatable member 120. At its distal tip, rotatable member 120 includes working element 122 which is optionally a dome-shaped instrument. Working element 122 includes curing blade 124 which aligns operatively with opening 123 of housing 110 in order to shear off material protruding through opening 123. In use, a vacuum is drawn on one or both of lumen 111 or lumen 121 and the opening in working element 122 is aligned with opening 123 on housing 110 in order to provide a continuous and open passage to receive mobile aortic plaque. Opening 123 is positioned so that such plaque is drawn into and through the opening, and held securely in place. Rotatable member 120 is then rotated to operate blade 124 on working element 122 so that blade 124 sweeps across the back surface of opening 123 and thereby shears off atheromatous plaque held through this opening. Excised plaque is drawn within lumen 121 and/or working element 122 by vacuum, and is held there to ensure that such materials do not escape as embolic material into the aortic or femoral artery blood stream. The use of a device as shown in FIG. 3 is depicted with mobile aortic plaque engaged through opening 123 in FIG. 5.

Figure 4:
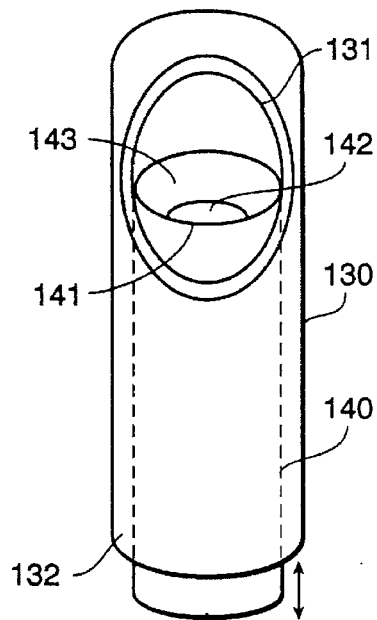
FIG. 4 depicts an atherectomy curing assembly for use in an arterial catheter system as disclosed herein.

In another embodiment, an atherectomy cutting assembly is provided at the end of flexible elongate tubular member 50 as depicted in FIG. 4. The atherectomy assembly includes housing 130 having inner lumen 132 and distal opening 131 adapted to receive mobile aortic plaque through such opening. In certain embodiments, opening 131 has fixed dimensions. In other embodiments (FIG. 4A), housing 130 includes adjustable orifice 131 which can be narrowed to opening 131A so as to grip plaque and hold plaque for cutting or pinching by the orifice. The assembly further includes elongate member 140 slidably received within lumen 132 of housing 130, and having distal edge 141 which is sharpened to act as a cutting blade. Circular blade 141 has a recessed interior which is in fluid communication with lumen 132 which extends through elongate member 140. In use, a vacuum is drawn on lumen 142 and member 140 is drawn proximal, such that blade 141 will not obstruct opening 131 of housing 130. Mobile aortic plaque is drawn through opening 131 by the influence of such vacuum, and member 140 is thereafter translated longitudinally and distally so that blade 141 sweeps across the edge of opening 131 and thereby excises atheromatous plaque extending through opening 131. Plaque debris thus excised is either compressed and deposited within the dome-shaped region at the distal tip of housing 130, or is drawn by suction into and through lumen 142.

Figure 4A:
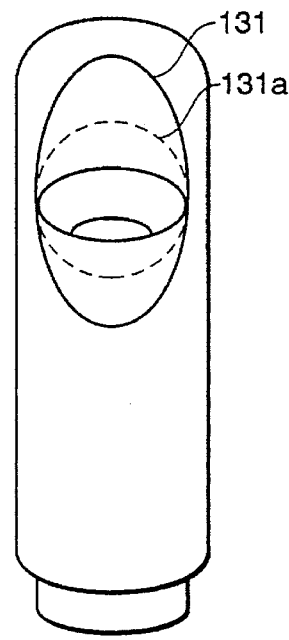
FIG. 4A depicts an atherectomy cutting assembly having an adjustable orifice.
Figure 13A:
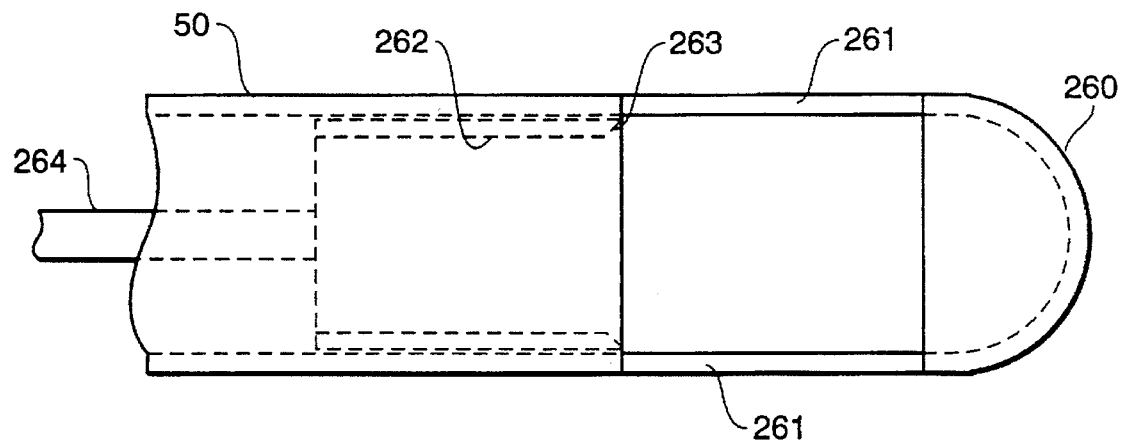
FIG. 13A depicts an atherectomy assembly in accordance with another embodiment, having more than one window to receive plaque material.
Figure 13B:
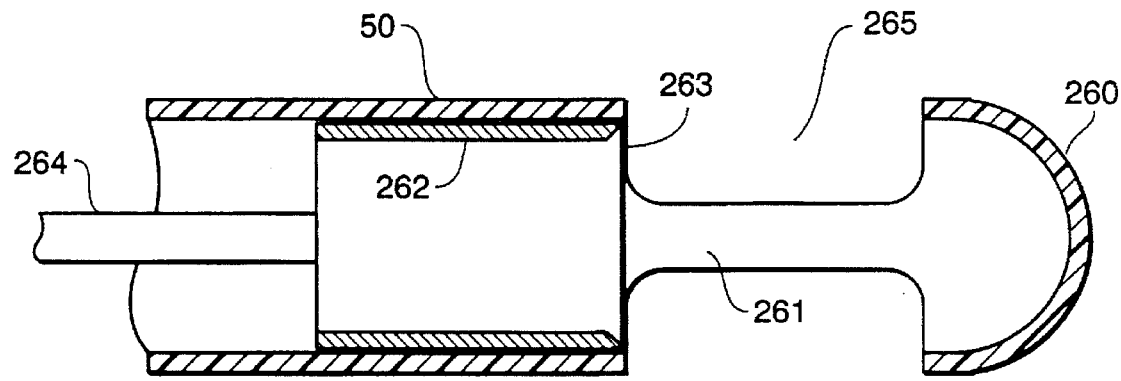
FIG. 13B depicts the atherectomy assembly of FIG. 13A viewed from above.
Figure 13C:
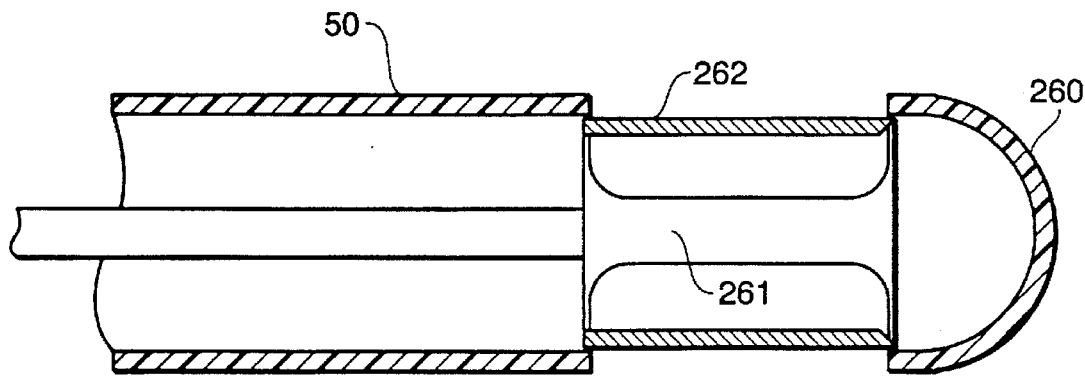
FIG. 13C depicts the atherectomy assembly of FIG. 13B with the cutting assembly translated to close off windows which receive plaque.

A variation on the side cutter shown in FIGS. 4 and 4A is depicted in FIGS. 13A, 13B, and 13C. With reference to FIG. 13B, catheter 50 includes at its distal end more than one opening 265 for plaque to enter. This feature renders the atherectomy assembly less sensitive to orientation and direction for receiving plaque material. Distal housing 260 is supported and connected to catheter 50 by a plurality of struts 261, which will typically comprise two, three, four, or more struts. A side view of struts 261 is shown in FIG. 13A. With reference to FIG. 13B, the catheter includes cutting blade 262 which is a generally cylindrical member having a sharpened distal edge 263 to cut plaque. In use, plaque material is received through side openings 265, and blade 262 is advanced distally, as shown in FIG. 13C, to excise the plaque.

Figure 14A:
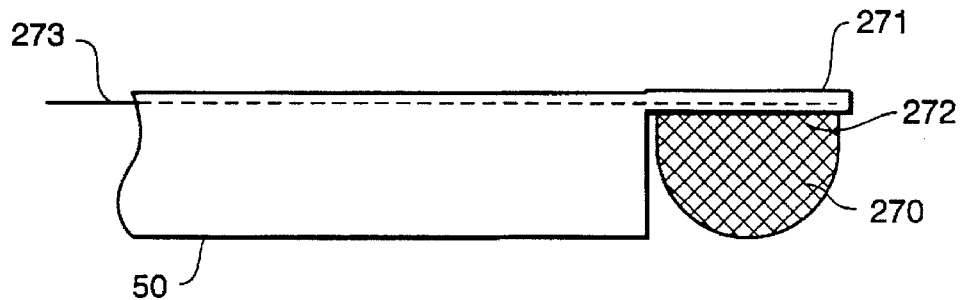
FIG. 14A depicts an atherectomy assembly in accordance with another embodiment, having a basket and a cutting wire or snare to excise plaque material.
Figure 14B:
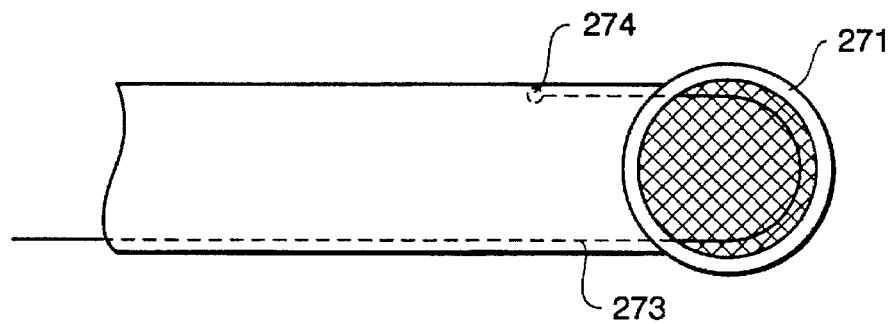
FIGS. 14B, 14C, and 14D show a top view of the atherectomy assembly depicted in 14A, with activation of a cutting wire to excise plaque.
Figure 14C:
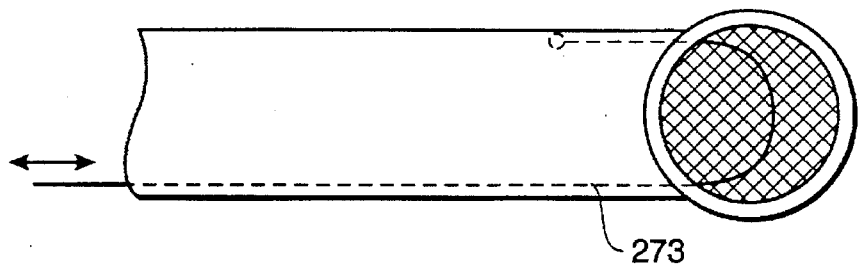
Figure 14D:
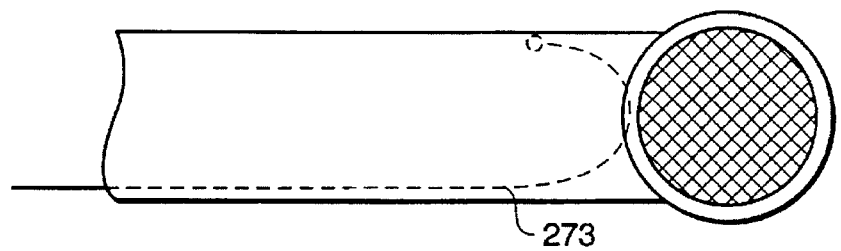

A further embodiment having a side cutter is shown in FIGS. 14A, 14B, 14C, and 14D. With reference to FIG. 14A, catheter 50 includes basket 270 attached to rim 271 at connection seam 272. FIG. 14B shows catheter 50 as viewed from above. The catheter further includes cutting wire or snare 273 which is attached at one end to post 274, and at its other end is operable from the proximal region of the catheter. Snare 273 extends into basket 270 and around the circumference of rim 271 before activation. Plaque material is received by the basket, and snare 273 is drawn in a proximal direction as shown in FIGS. 14C and 14D in order to excise plaque during use.

In another embodiment, a basket side cutter is provided as shown in FIGS. 16A, 16B, 16C, and 16D. With reference to FIG. 16B, catheter 50 includes pivot member 293 extending from a distal end thereof. Semicircular rims 290 and 292 are pivotally connected to member 293, and each rim carries a basket 291A and 291B. FIGS. 16C and 16D show a view of the catheter from the distal end. In use, the rims and baskets are operated to close about a plaque, and excise the plaque by pinching or cutting. Plaque material, once removed, falls into the closed basket, and thereafter presents no risk of embolization. The basket can be removed from the patient while closed, or the plaque can be drawn into the catheter housing and stored therein. Thereafter, the basket can be reopened to perform atherectomy on another plaque.

Figure 6:
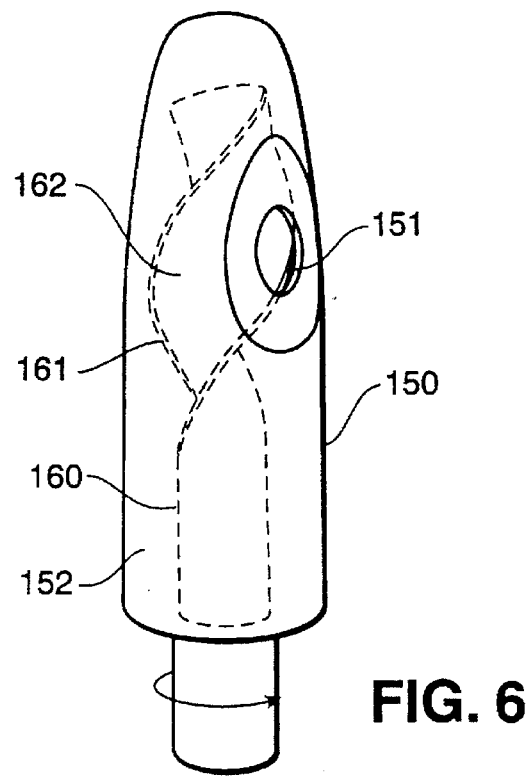
FIG. 6 depicts an atherectomy cutting assembly for use in an arterial catheter system as disclosed herein.

In another embodiment, an atherectomy assembly is provided at the distal region of flexible elongate member 50 as depicted in FIG. 6. The atherectomy assembly includes housing 150 having inner lumen 152 and side opening 151 disposed about the distal region of housing 150. Lumen 152 is adapted to receive elongate member 160 which is twisted in a helical manner about its distal region 162. Edge 161 of member 160 is sharpened to provide a cutting blade which is capable of shearing atheromatous plaque when positioned to engage such plaque. Thus, in use, a vacuum is drawn on lumen 152, and this suction will pull mobile aortic plaque into and through opening 151. Member 160 is then operated by rotation to bring blade 161 into contact with the engaged mobile aortic plaque, and to sweep across opening 151, thereby excising the plaque which is securely held within housing 150.

Figure 7:
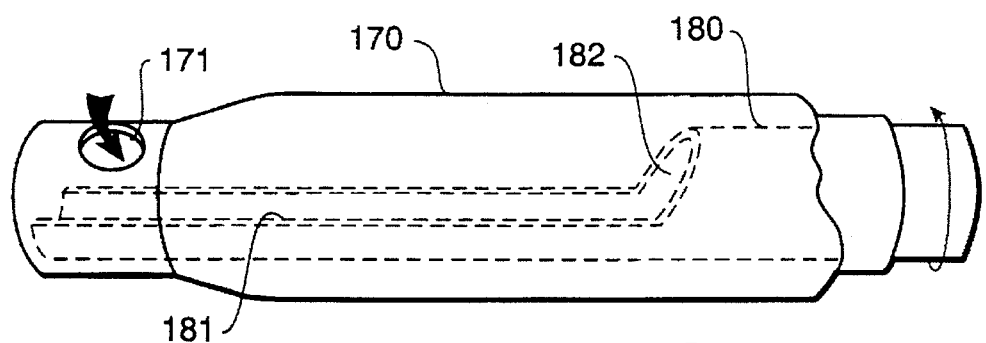
FIG. 7A depicts a cutting blade which is received by the housing of FIG. 7 to comprise a cutting assembly for use in an arterial catheter system as disclosed herein.
Figure 7A:
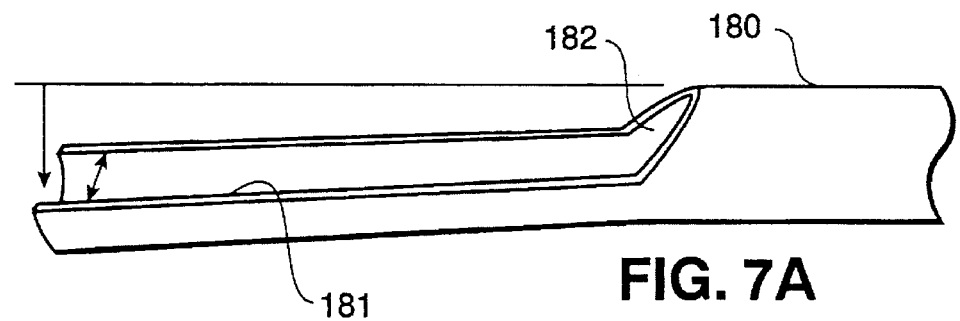

In another embodiment, an atherectomy assembly is provided as depicted in FIG. 7. The assembly includes housing 170 having opening 171 in a distal region 180 and adapted to receive mobile aortic plaque from within an artery. Rotatable member 180 is disposed within the lumen of housing 170, the rotatable assembly having lumen 182 and a semicircular portion of the cylindrical member cut away in the distal region. The semicircular region includes cutting blade 181 which can be sharpened to cut atheromatous plaque. With reference to FIG. 7A, rotatable member 180 includes, at its distal extremity, a region which is angled to deflect away from the longitudinal centerline of member 180. When disposed within the lumen of housing 170, the angle of deflection in member 180 ensures that blade 181 is biased against the lumen of housing 170 and thereby ensures a snug fit. In use, a suction is drawn through lumen 182 which secures plaque in a region of interest through opening 171. Member 180 is then rotated to bring blade 181 into contact with the mobile aortic plaque drawn through opening 171. Plaque material is thereby shaven from the aorta, and the snug fit between blade 181 and the lumen of housing 170 allows maximization of the amount of plaque material excised.

Figure 8:
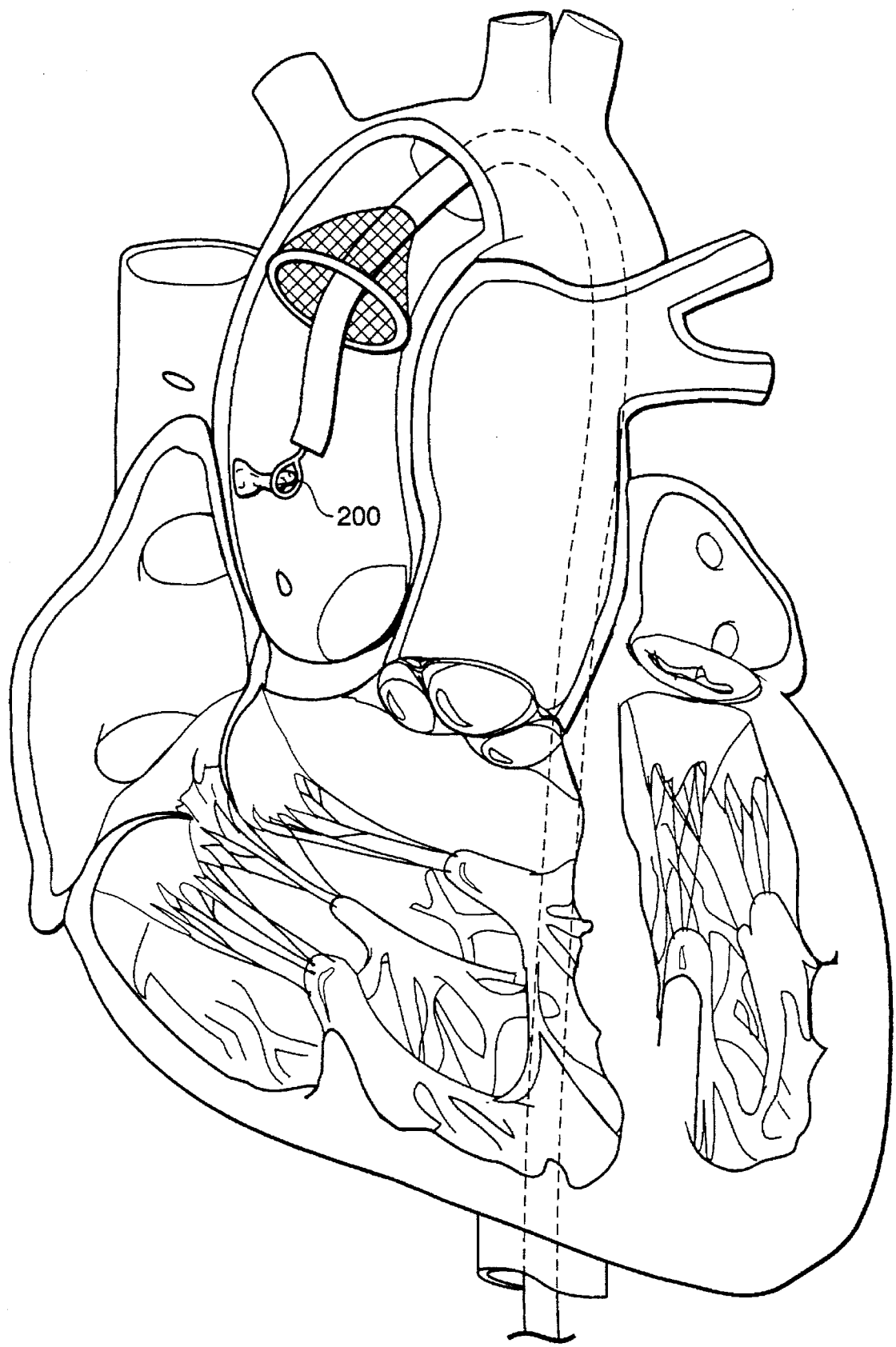
FIG. 8 is a longitudinal view of an arterial catheter system having its distal end positioned in the ascending aorta, and using a snare as a trapping mechanism for mobile aortic plaque.

Another embodiment having a snare as a trapping mechanism is depicted in FIG. 8. This figure shows an atherectomy filtration catheter having snare 200 disposed in the distal region thereof. Snare 200 is positioned over a plaque and thereby engages the plaque, holding it in place. The distal tip of the catheter is then advanced distally while holding the snare fixed. In this manner, the snare is used to maneuver the fixed or mobile plaque into the tip of the catheter. Once the plaque is secured within the catheter tip, the plaque can be excised and retained within the catheter, with or without the assistance of suction. Thus, the plaque can be excised by the snare, or by a cutting assembly disposed within the distal tip of the catheter.

Thus far, we have described in FIGS. 3–7 a number of excising means which are adapted to receive plaque through a side opening in the cutting assembly. FIG. 9A shows an alternative embodiment which is oriented to receive plaque material through an end opening. Catheter 50 includes basket 221 attached at seam 220 to the catheter distal end. The distal region of basket 221 is attached to a contracting loop or inflation member 222 which is secured to catheter 50 by support wires 223. In use, the contracting loop is narrowed as shown in FIG. 9B after receiving a plaque through the distal opening. Loop 222 narrows about the plaque, and pinches the plaque as an excising mechanism, and the plaque falls into, and is securely retained by basket 221.

Figure 11A:
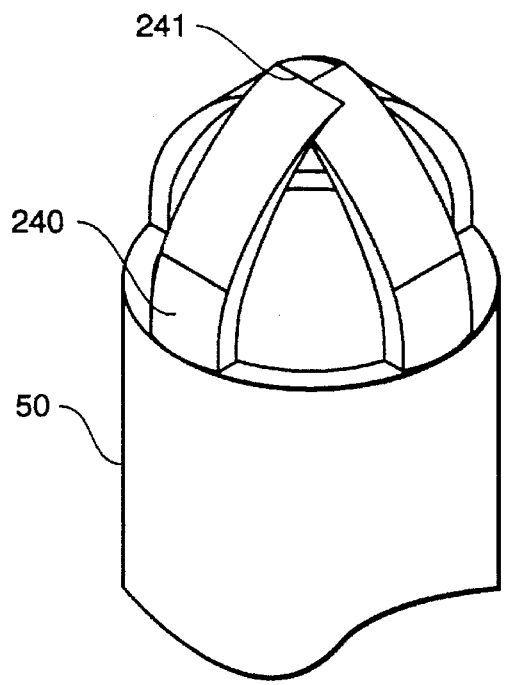
FIG. 11A depicts an atherectomy assembly in accordance with another embodiment, and having claws which operate to grab plaque material.
Figure 11B:
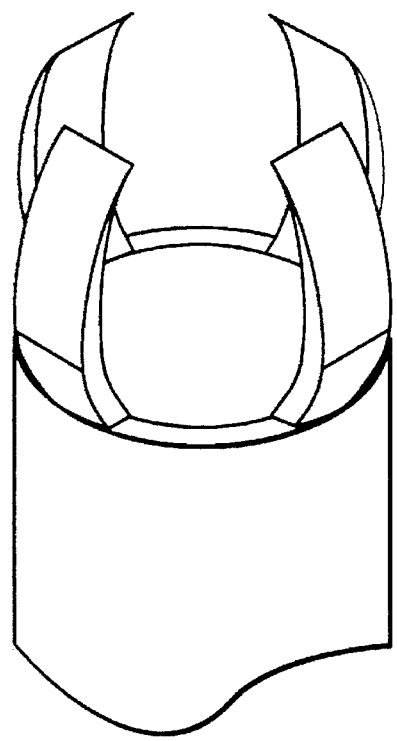
FIG. 11B depicts the atherectomy assembly of FIG. 11A, in an open condition.
Figure 12A:
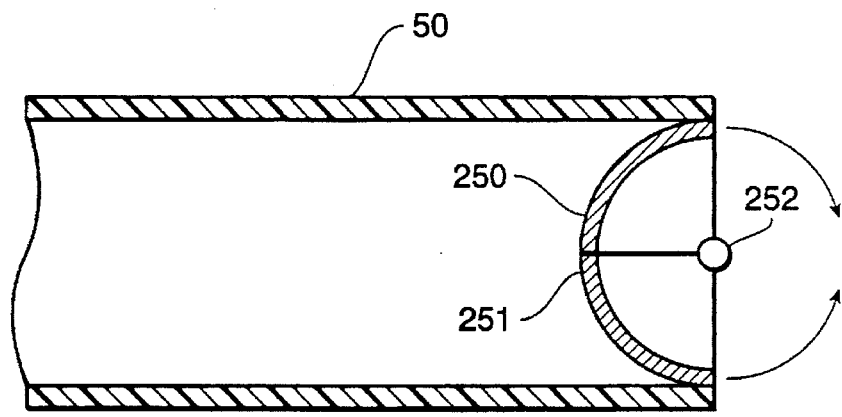
FIG. 12A depicts an atherectomy assembly in accordance with another embodiment, having partial spherical surfaces which pivot to close upon plaque material.
Figure 12B:
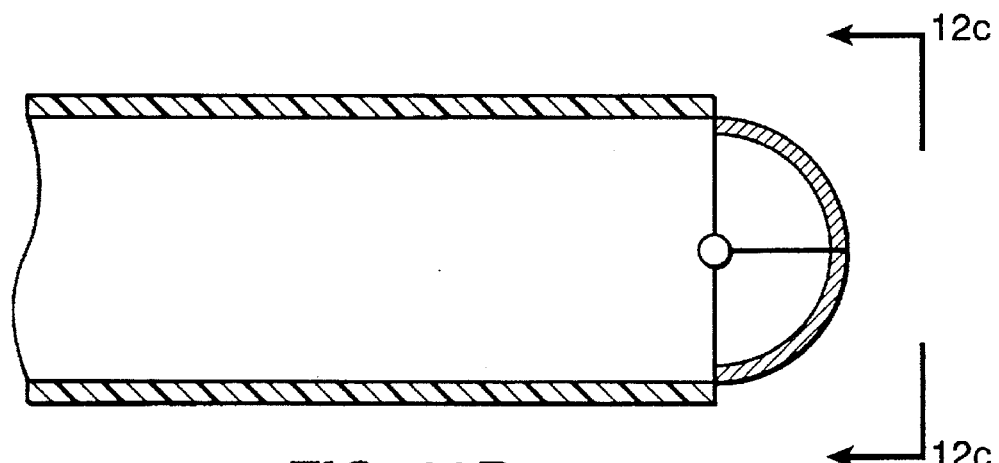
FIG. 12B depicts the atherectomy assembly of FIG. 12A in the closed condition.
Figure 12C:
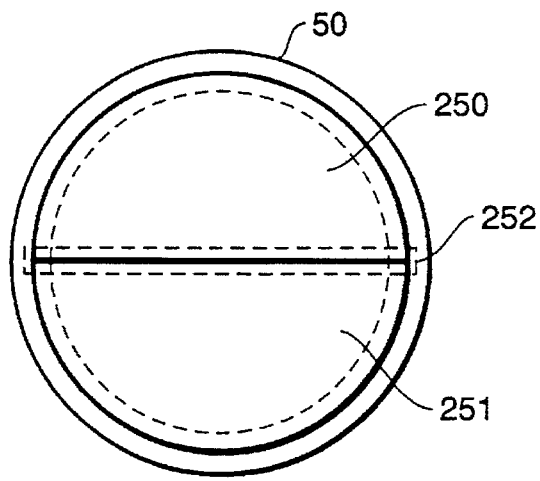
FIG. 12C depicts the atherectomy assembly of FIG. 12B as viewed from its distal tip.
Figure 15A:
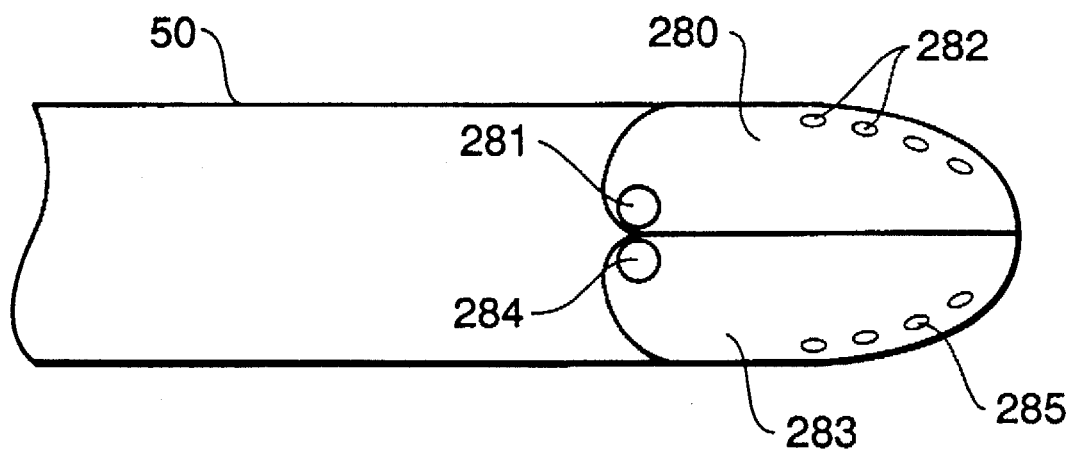
Figure 15B:
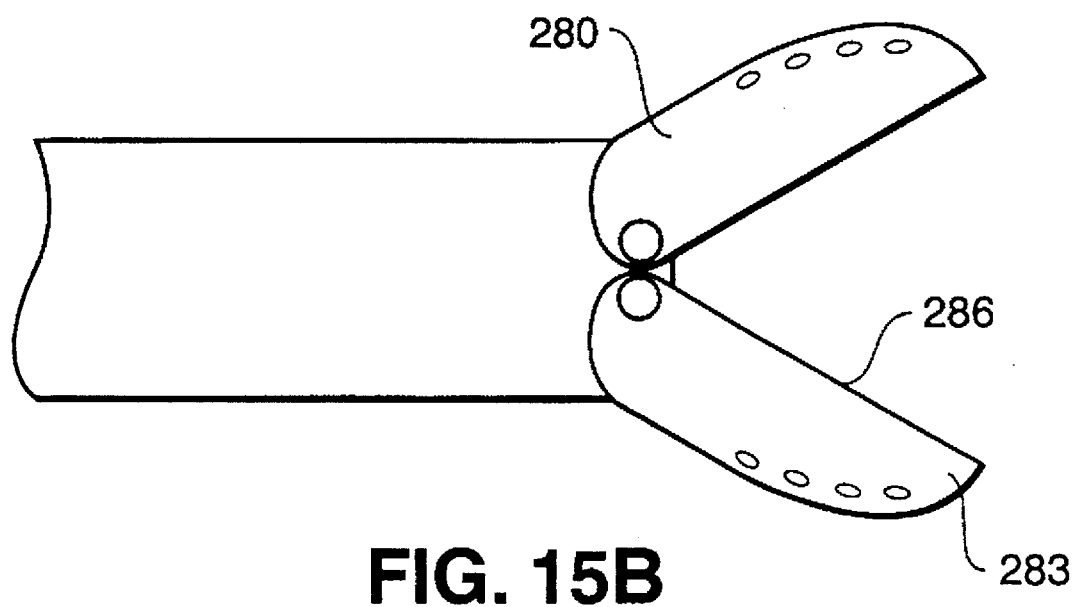
FIG. 15B depicts the atherectomy assembly in an open configuration.

Another device which receives plaque through the distal end is depicted in FIG. 10. Housing 230 is attached to the distal end of catheter 50, and the housing terminates at distal surface 231. Surface 231 includes adjustable orifice 232 which is shaped to receive plaque when enlarged, and to thereafter narrow around the plaque material. Once trapped, the plaque is excised, either by pinching or by shearing with cutting blade 233. FIG. 11A shows an alternative distal cutting assembly, having claws 240 with sharpened distal edges 241 which can be operated to trap and remove plaque. This device receives plaque in its open configuration, depicted in FIG. 11B. In another embodiment, a device is provided as shown in FIG. 12A which receives plaque through a distal end opening. This device includes one or two substantially semispherical members 250 and 251 which are attached to, and pivot about axis member 252. As shown in FIG. 12B, and in cross-section in FIG. 12C, the semispherical members are pivoted about axis 252 in order to clamp down on plaque at the distal end of catheter 50. Accordingly, the semispherical component may have sharpened edges where they meet when closed, in order to pinch off plaque and capture the debris within the housing of catheter 50. In a further embodiment shown in FIGS. 15A and 15B, catheter 50 is equipped with clam shell members 280 and 283 which are pivotally coupled to catheter 50 by axis members 281 and 284. Clam shells 280 and 283 may have sharpened edges to close on, and excise plaque, and may include perforations 282 and 285 to permit blood flow out of the device when the clam shells are closed.

Figure 22:
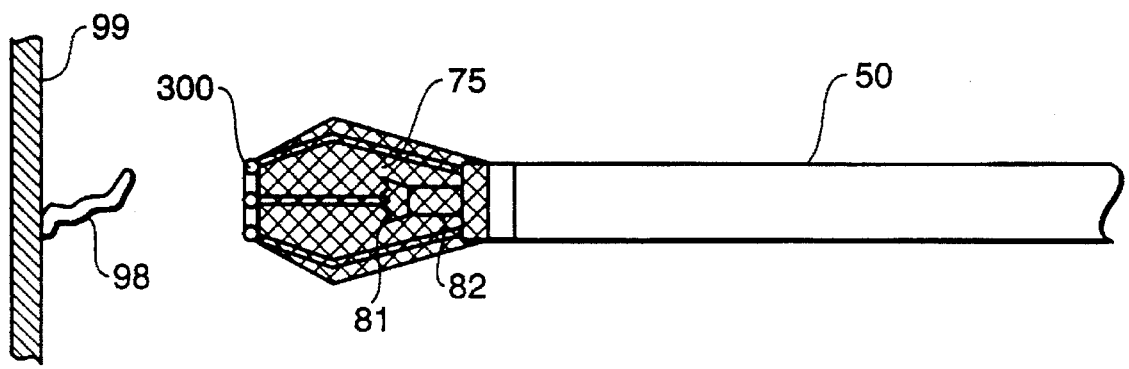
FIGS. 22 and 22A depict an atherectomy catheter having clamping fingers and associated mesh for forward removal of plaque.
Figure 22A:
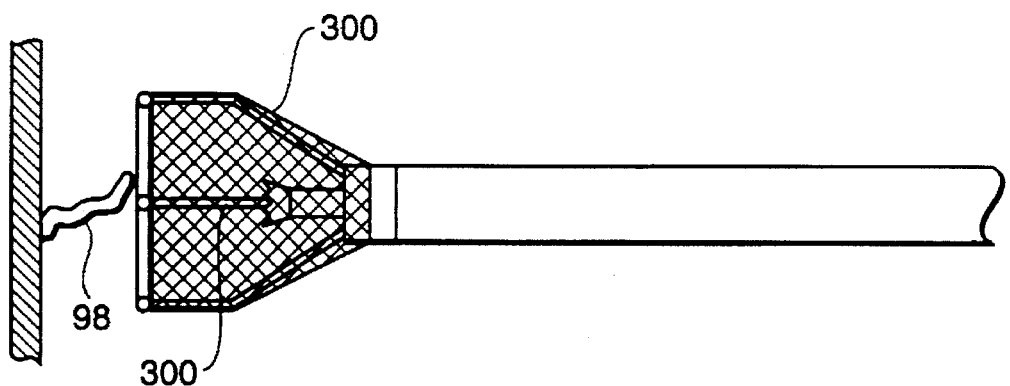

In another embodiment, an atherectomy catheter is provided as depicted in FIGS. 22 and 22A. Catheter 50 includes at its distal end a plurality of clamping fingers 300 which are operable between an open and closed condition. A fine filtration mesh 75 is disposed over fingers 300 and is positioned to capture embolic material dislodged during atherectomy. The atherectomy assembly further includes cutter 81 and suction lumen 82 which remove plaque debris 98 loosely attached to the aorta, common carotid artery, external and internal carotid arteries, brachiocephalic trunk, middle cerebral artery, anterior cerebral artery, posterior cerebral artery, vertebral artery, basilar artery, subclavian artery, brachial artery, axillary artery, iliac artery, renal artery, femoral artery, popliteal artery, celiac artery, superior mesenteric artery, inferior mesenteric artery, anterior tibial artery, posterior tibial artery and all other arteries carry oxygenated blood. In use, catheter 50 approaches plaque 98 with open fingers 300 as depicted in FIG. 22A. Fingers 300 and mesh 75 are closed about plaque 98, and plaque 98 is engaged by cutter 81. Suction is applied to lumen 82 to remove fine debris resulting from the atherectomy procedure.

Figure 17:
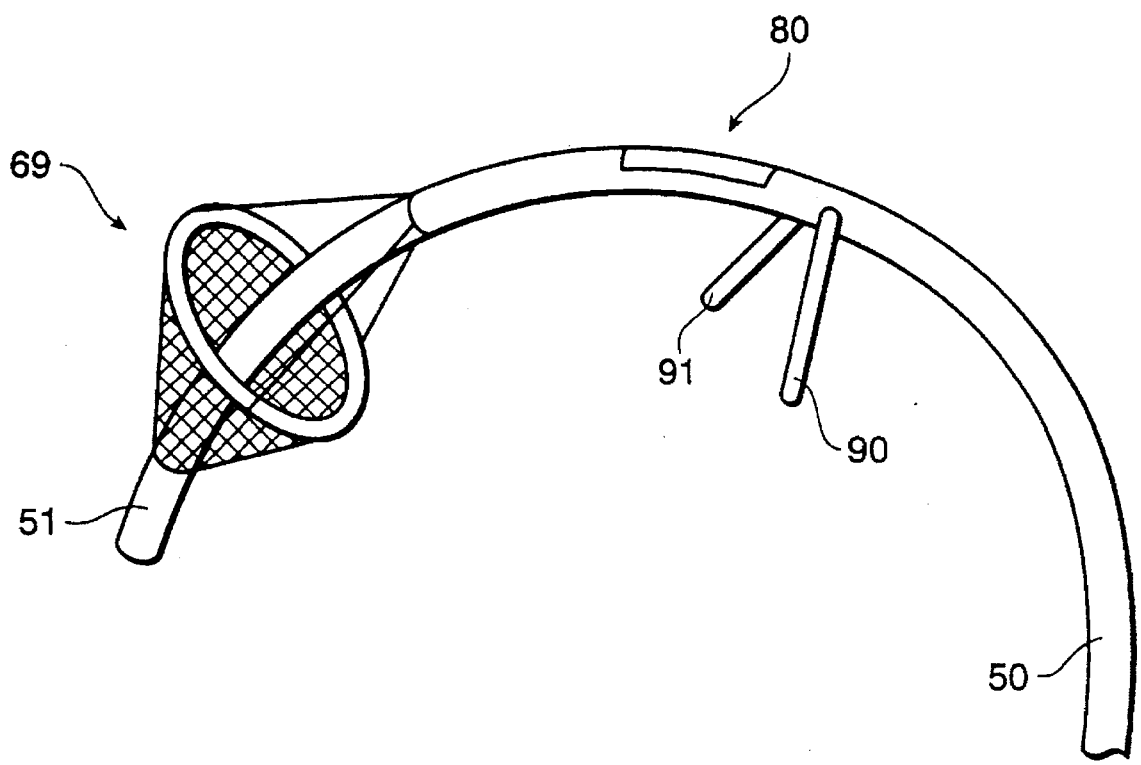
FIG. 17 is a longitudinal view of an arterial catheter system for use in the carotid arteries.

In another embodiment, a carotid/vertebral artery atherectomy catheter is provided as depicted in FIG. 17. Catheter 50 includes filtration assembly 69 disposed in distal region 51. It will be understood that, during use, the catheter is inserted and guided upwardly through the descending aorta until it reaches the aortic arch, whereupon the catheter is guided into one of the carotid arteries, which include the brachiocephalic trunk, the right common carotid artery, the right internal and external carotid arteries, the left common carotid artery, the left internal and external carotid arteries, the right subclavian artery, the left subclavian artery, and the right and left vertebral arteries. In these vessels, blood flow relative to the site of atherectomy is toward the distal end of catheter 50. Accordingly, filtration assembly 69 is inverted and disposed distally to atherectomy assembly 80 on the catheter of FIG. 17. As noted above, atherectomy assembly 80 may further include suction means, cutting means, and visualization means. The catheter may also be equipped with one or more deployable positioning fingers 90 and 91 which act to bias the catheter in the lumen of the carotid artery toward a plaque within the region of interest. Positioning fingers 90 and 91 may comprise a mechanical projecting finger or one or more elastomeric balloons which are inflatable through one or more separate lumens within catheter 50.

Figure 18:
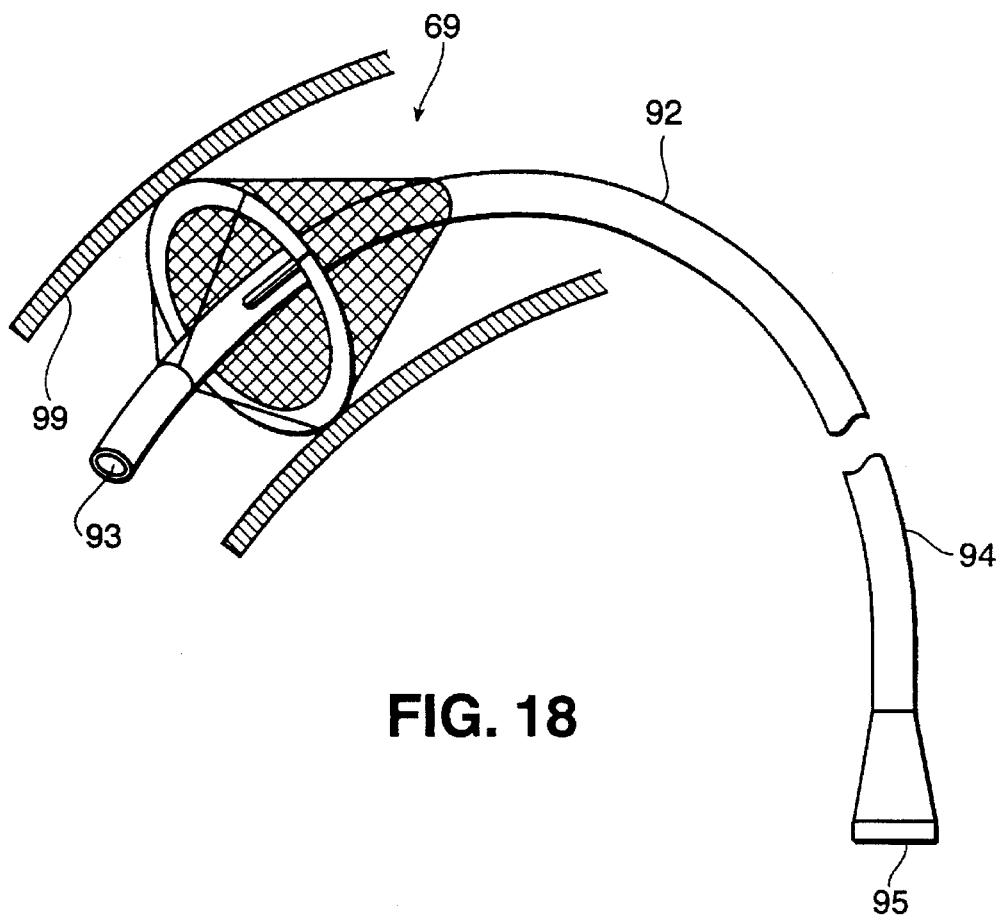
FIG. 18 depicts a filtering and positioning atherectomy guide catheter.
Figure 19:
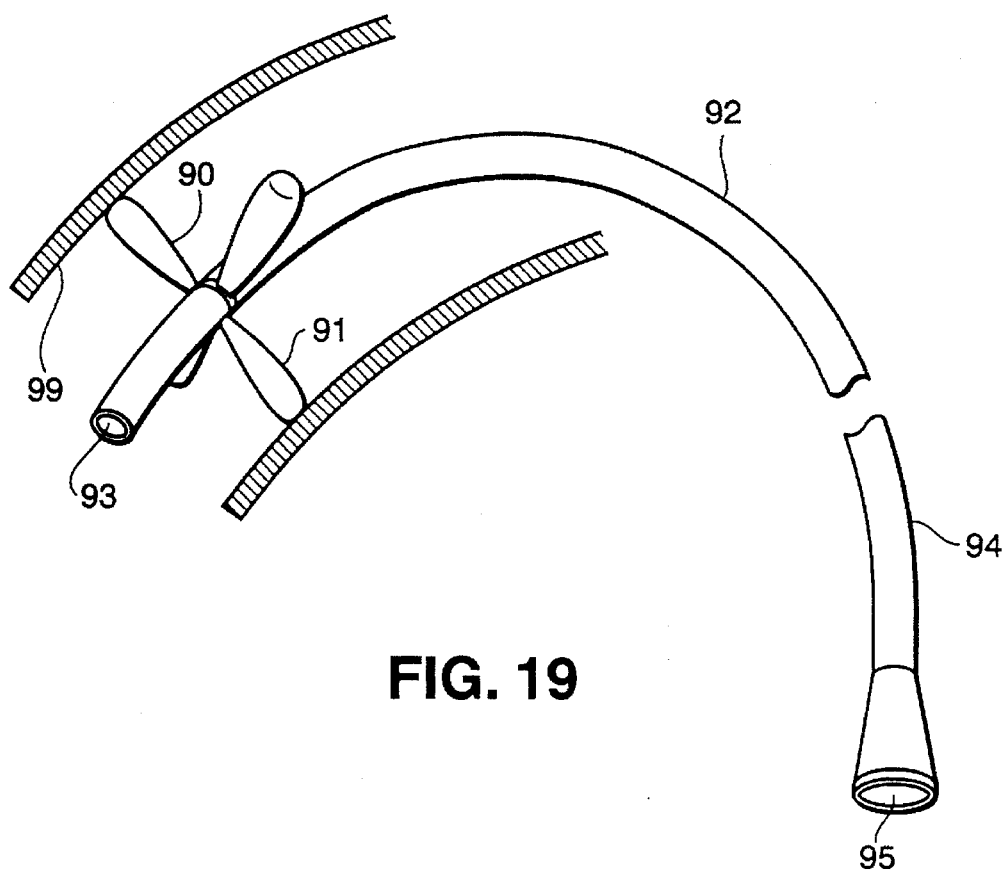
FIG. 19 depicts a positioning atherectomy guide catheter.

In another embodiment, a guiding catheter is used to position and stabilize the atherectomy catheter within the vessel in a region of interest, as shown in FIGS. 18 and 19. With reference to FIG. 18, guiding catheter 92 may carry filtration assembly 69 and allow passage of the atherectomy catheter through lumen 93. The atherectomy catheter is therefore free of filtration, and can be operated without moving the filter. Guide catheter 92 includes proximal region 94 adapted for percutaneous insertion, and further includes hemostatic valve 95 at its proximal end. In use, the guiding catheter will be positioned and its filter deployed. In a separate step, the atherectomy catheter will be advanced through the guiding catheter and operated out of a distal opening. In other embodiments, the guiding catheter will have a bend (not shown) in its distal tip which will direct the atherectomy catheter toward the aortic wall.

The guiding catheter may also be a positioning atherectomy guide catheter which has deployable positioning fingers disposed circumferentially around the guiding catheter to center the guiding catheter in a vessel, or to bias the catheter to one side, as depicted in FIG. 19. Guiding catheter 92 includes lumen 93 adapted to receive an atherectomy catheter which, in this case, may also include a deployable filtration system since guiding catheter 92 does not carry filtration capabilities. One, two, three, four, or more positioning fingers 90 and 91 are included on the distal region of guide catheter 92, and may be comprised of mechanical expanding struts or elastomeric or non-elastomeric balloons inflatable by one or more inflation lumens. Thus, a filter (FIG. 18) and/or deployable struts (FIG. 19) can center the guide catheter and thereby provide a stable platform from which to operate the atherectomy catheter or can be used to bias a guide catheter toward a plaque.

Figure 20:
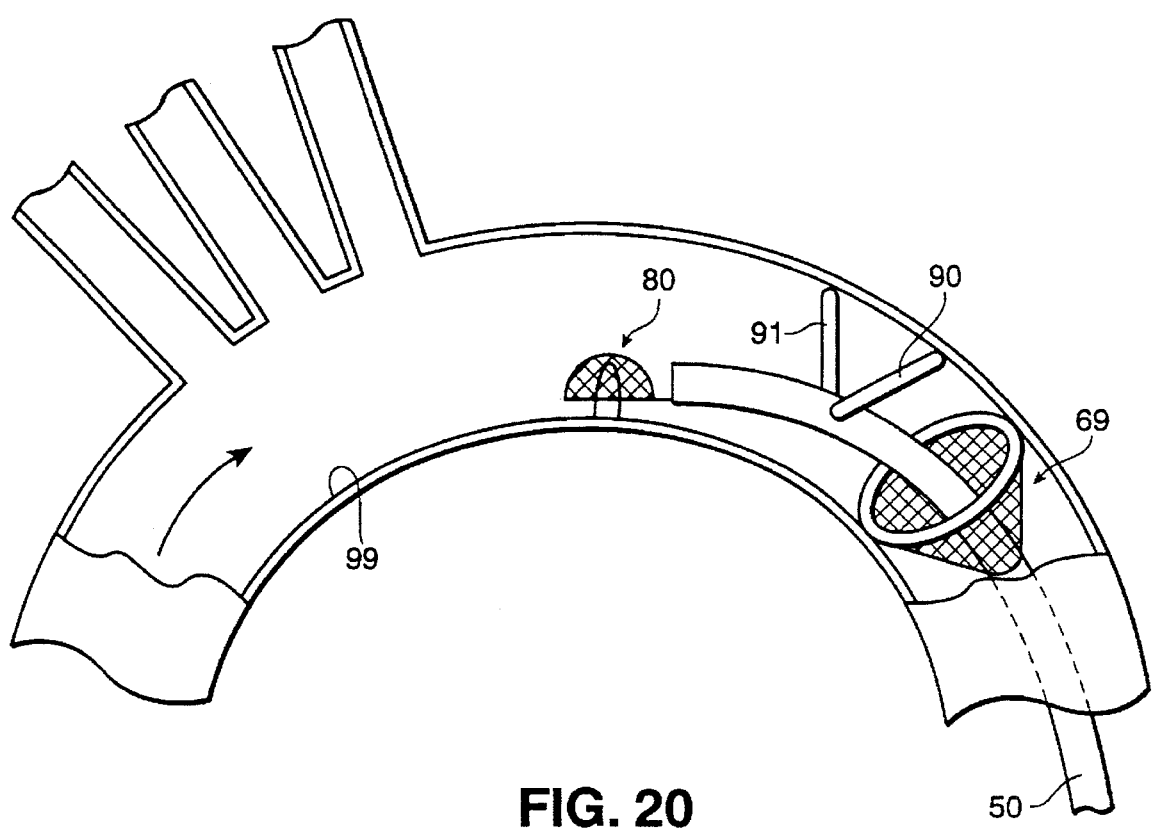
FIG. 20 depicts an atherectomy catheter having an atherectomy assembly as shown in FIGS. 14A–14D, including positioning struts.
Figure 21:
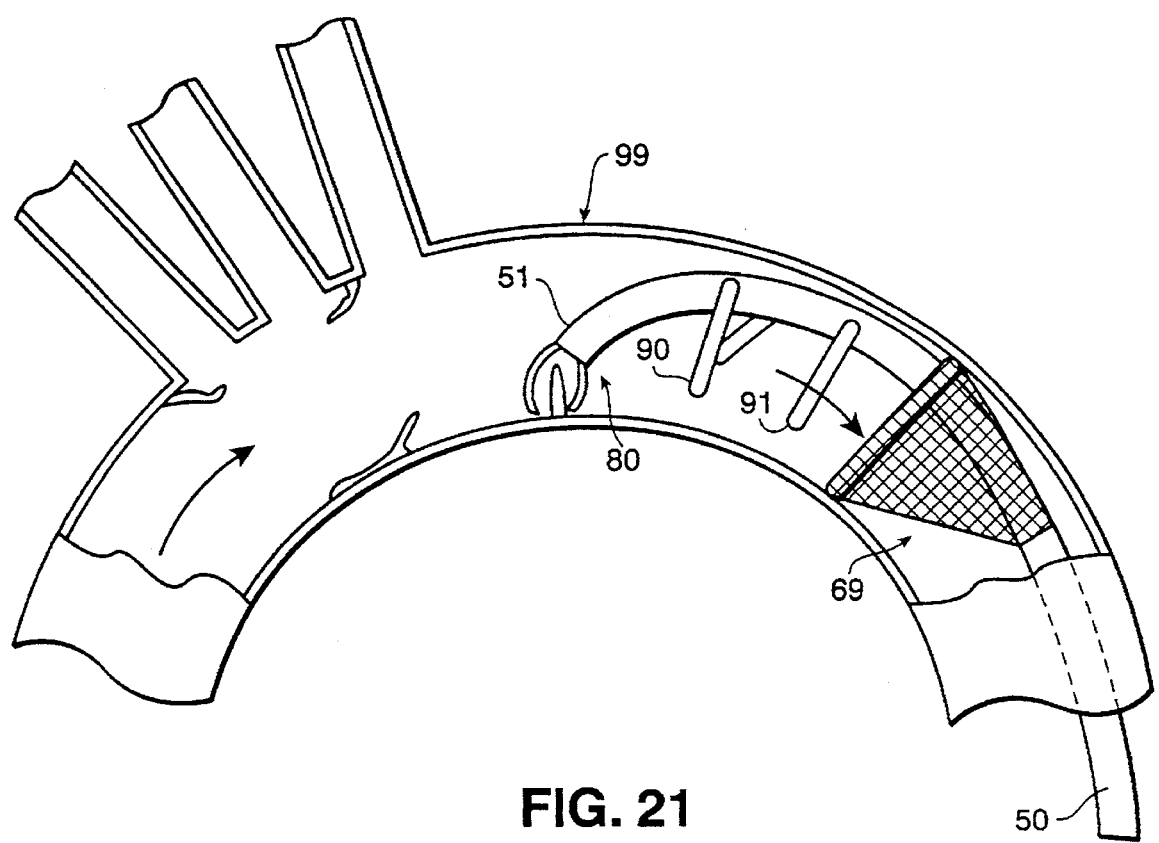
FIGS. 21 and 21A depict an atherectomy catheter deployed in the aortic arch and using positioning struts to deflect away from plaque.
Figure 21A:
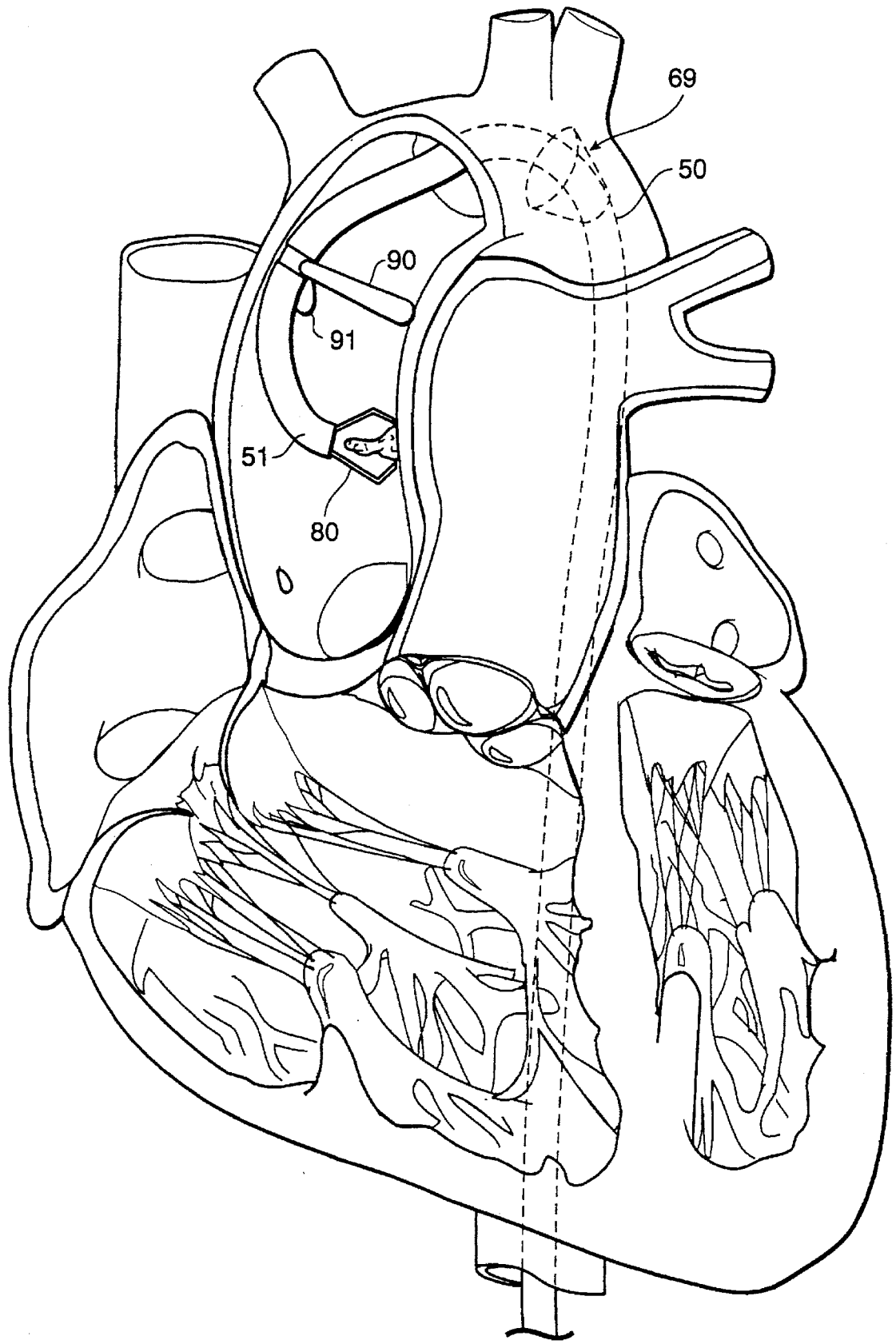

Deployable positioning fingers can also be used to center or bias an atherectomy catheter when used without a guide catheter. FIG. 20 depicts catheter 50 having filtration assembly 69 and atherectomy assembly 80 deployed within aorta 99 and engaged about a plaque. Catheter 50 further includes deployable positioning members 90 and 91 which, when deployed, bias atherectomy assembly 80 toward the plaque material. In another embodiment, one or more biasing members 90 and 91 displace the catheter away from the center of the arterial lumen and to a direction away from the plaque material, as shown in FIG. 21. Catheter 50 includes steering capabilities within its distal region which allow the catheter to bend toward the region of interest and thereby bring atherectomy assembly 80 into contact with a plaque. Thus, biasing members 90 and 91 position the shaft of catheter 50 in a manner which allows adequate room for bending of distal region 51 without having to turn a sharp corner.

Figure 23:
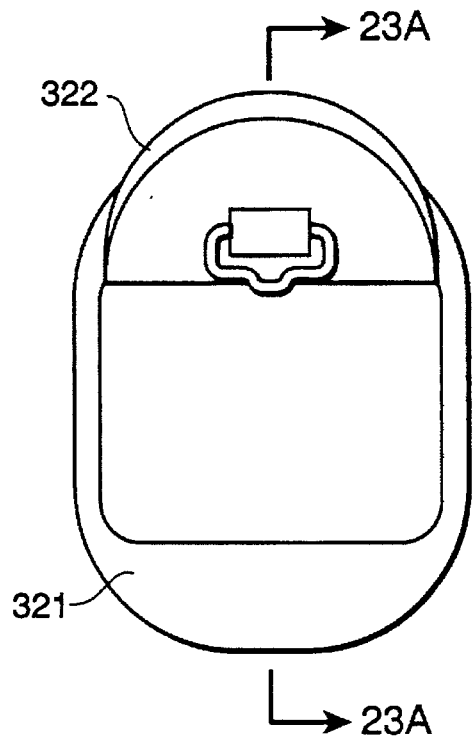
FIGS. 23 and 23A depict an atherectomy catheter having plaque retention means.
Figure 23A:
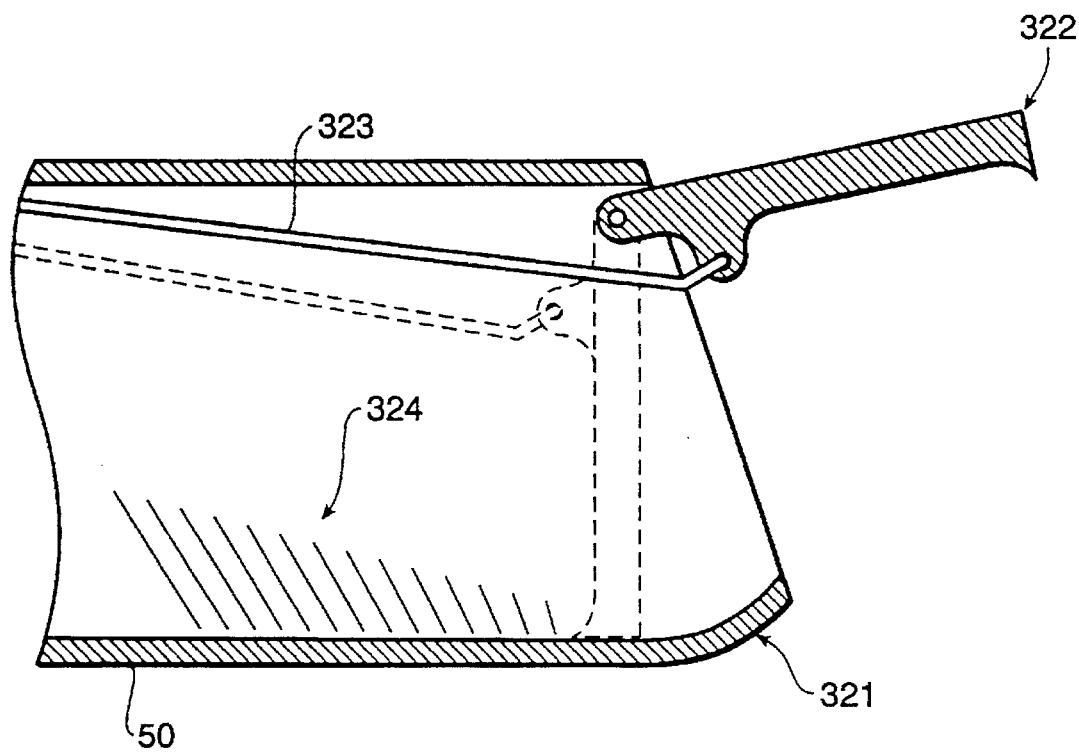

In another embodiment, the catheter provides a biopsy-like tool as depicted in FIGS. 23 and 23A. With reference to FIG. 23, the atherectomy catheter includes housing 321 at its distal end and shear 322 which is pivotally connected to housing 321. A side view of the catheter is shown in FIG. 23A. Shear 322 is operated by actuator 323. Housing 321 further includes particle trapping material 324 such as particle trapping filaments which hold excised plaque material in place so that it may not escape into the circulation when shear 322 is reopened. In use, the housing receives a plaque through its distal opening. Actuator 323 is operated proximally to pull shear 322 inward, thereby cutting the plaque. As shear 322 carries inward, it sweeps the plaque into the housing where it becomes engaged by particle trapping filaments 324. The distal opening is then reopened to receive and excise another plaque, whereby plaque material builds up on, but does not escape from, housing 321.

An aortic or femoral artery atherectomy procedure is conducted by deploying the arterial atherectomy catheter through the femoral artery in accordance with procedures well known in the art for coronary atherectomy. The atherectomy catheter of FIG. 2 is advanced up the femoral artery and optionally up the descending aorta until the catheter reaches the region of interest. One or more fluoroscopic markers may be included on the distal region of the catheter to permit fluoroscopic visualization of the catheter as it advances on its path. The atherectomy assembly is localized in the region of interest, and may be positioned with guidance from any of a number of visualization techniques previously discussed. Means for visualization are especially important where the atherectomy catheter must be guided around and through the aortic arch. Moreover, a conventional guidewire and/or guiding catheter can be used to assist the maneuvering of the atherectomy catheter through the artery of interest. Once the catheter is located in the region of interest, the filtration mechanism is activated to expand the filter so that substantially the entire cross-section of the vessel is covered by filter. An opening on the atherectomy assembly is positioned in close proximity to atheromatous plaque material, typically mobile aortic plaque, and a vacuum is applied to one or more lumen of the catheter in order to draw plaque material into the opening. The vacuum functions both to securely hold the plaque material in place, and to ensure that materials dislodged during the cutting procedure are retained within the catheter device, and do not escape to form emboli. A cutting blade or means for cutting is then activated to excise plaque secured by vacuum. Once the atherectomy procedure has been completed, the catheter may be repositioned to excise additional plaque, or withdrawn from the vessel. In either case, the filtration means will be contracted to reduce its size and thereby allow movement within the vessel without scraping against the lumen of the aorta. The catheter is thereafter either repositioned longitudinally or withdrawn from the vessel to complete the procedure in accordance with methods known in the art. Notably, all plaque material excised during this procedure remains trapped either within the catheter housing under suction, or within the filtration mesh once collapsed.

In this manner, the patient is protected from embolization during an aortic atherectomy procedure.

While particular devices and methods have been described for performing atherectomy and filtering blood, once this description is known, it will be apparent to those of ordinary skill in the art that other embodiments and alternative steps are also possible without departing from the spirit and scope of the invention. Moreover, it will be apparent that certain features of each embodiment as well as features disclosed in each reference incorporated herein, can be used in combination with devices illustrated in other embodiments. Accordingly, the above description should be construed as illustrative, and not in a limiting sense, the scope of the invention being defined by the following claims.

What is claimed is:

1. An arterial catheter system for removing plaque from the aorta or other arteries, said catheter system comprising:

a flexible elongate member having an outer surface, a distal region adapted to enter an artery, and a proximal region;

expansion means disposed within the distal region of the elongate member which is expandable between a contracted condition and an enlarged condition;

a mesh having a first edge attached circumferentially and continuously to the expansion means and a second edge disposed circumferentially about and in contact with the outer surface of the flexible elongate member; and an atherectomy assembly disposed within the distal region of the elongate member, the atherectomy assembly comprising means for plaque removal and trapping means, wherein during use said first edge of said mesh is positioned at a distance from the outer surface of the flexible elongate member, and said plaque is trapped and held by the trapping means and excised from the arterial lumen by the means for plaque removal.

2. The arterial catheter of claim 1, wherein the expansion means comprises an umbrella frame having a plurality of arms which, upon activation, bend outwardly to the enlarged condition.

3. The arterial catheter of claim 1, further comprising one or more positioning fingers disposed within the distal region of the elongate member.

4. The arterial catheter of claim 1, wherein the flexible elongate member is equipped with steering capabilities.

5. The arterial catheter of claim 1, wherein the flexible elongate member extends through the mesh.

6. The arterial catheter of claim 1, wherein the flexible elongate member includes a housing having a cavity adapted to receive and store excised plaque material.

7. The arterial catheter of claim 1, wherein the expansion means comprises an inflation seal.

8. The arterial catheter of claim 7, wherein the trapping means comprises a suction device.

9. The arterial catheter of claim 7, wherein the means for plaque removal comprises a cutting blade.

10. The arterial catheter of claim 7, in the flexible elongate member further includes an inflation system comprising a first lumen adapted to receive pressurized fluid and a second lumen adapted to evacuate gas, and wherein the inflation seal further includes an entry port in fluid communication with the first lumen of the flexible elongate member and an exit port in fluid communication with the second lumen of the flexible elongate member, so that when fluid is advanced through the first lumen, the fluid enters the inflation seal and forces gas from the inflation seal through the second lumen, thereby purging the system of gas.

11. The arterial catheter of claim 10, wherein the inflation seal comprises a tubular balloon which encloses a chamber, and wherein the entry port and exit port are in close proximity, and wherein a septum is disposed between the entry and exit ports.

12. The arterial catheter of claim 7, further comprising a plurality of holding strings which attach the inflation seal to the flexible elongate member.

13. The arterial catheter of claim 7, wherein the trapping means comprises a snare.

14. The arterial catheter of claim 7, wherein the trapping means comprises a surface having an adjustable orifice.

15. The arterial catheter of claim 7, wherein the means for plaque removal comprises a snare.

16. The arterial catheter of claim 7, wherein the means for plaque removal comprises a surface having an adjustable orifice.

17. The arterial catheter of claim 7, wherein the means for plaque removal comprises a basket having an adjustable opening adapted to close about the plaque and excise a portion of the plaque by pinching.

18. The arterial catheter of claim 7, wherein the means for plaque removal comprises a plurality of claws which are movable between an open and a closed position.

19. The arterial catheter of claim 7, wherein the means for plaque removal comprises first and second substantially semispherical surfaces pivotally connected to the elongate member and movable between an open and closed position.

20. The arterial catheter of claim 7, wherein the means for plaque removal comprises a basket and a cutting wire having a first end anchored to the elongate member and a second end which is drawn in a proximal direction, wherein a segment of the cutting wire sweeps across the opening to the basket during operation.

21. The arterial catheter of claim 1, wherein the atherectomy assembly is disposed within the distal region of the elongate member and distal to the expansion means and mesh.

22. The arterial catheter of claim 1, wherein the atherectomy assembly is disposed within the distal region of the elongate member and proximal to the expansion means and mesh.

23. A method for removing plaque from the aorta or other arteries of a patient, comprising the steps of:

providing an arterial catheter system comprising a flexible elongate member having an outer surface, a distal region adapted to enter an artery, a proximal region, an atherectomy assembly disposed within the distal region of the elongate member, the atherectomy assembly comprising means for plaque removal and trapping means, and a filtration system comprising expansion means disposed about the distal region of the elongate member which is expandable between a contracted condition and an enlarged condition, and a mesh having a first edge attached circumferentially and continuously to the expansion means and a second edge disposed circumferentially about and in contact with the outer surface of the flexible elongate member;

introducing the distal region of the arterial catheter into a region of interest within the patient's artery, through an incision in the femoral or brachial artery;

deploying the filtration system downstream of the plaque within the artery by expanding the expansion means until said first edge of said mesh is positioned at a distance from the outer surface of the flexible elongate member and said first edge achieves contact with the lumen of the artery;

contacting the atherectomy assembly with the plaque within the artery, wherein the plaque is trapped and held by the atherectomy assembly by use of the trapping means;

excising the plaque from the artery by operating the means for plaque removal while simultaneously operating the trapping means to secure the plaque;

contracting the expansion means to the contracted condition; and removing the arterial catheter system and the plaque entrapped therein from the region of interest and the femoral artery.

24. The method of claim 23, wherein the region of interest is within the patient's aorta, and wherein the filtration system is disposed within the distal region of the flexible elongate member and proximal to and downstream of the atherectomy assembly.

25. The method of claim 23, wherein the region of interest is within the patient's carotid artery, and wherein the filtration system is disposed within the distal region of the flexible elongate member and distal to and downstream of the atherectomy assembly.

26. The method of claim 23, wherein the step of contacting the atherectomy assembly with the plaque includes the step of deploying one or more positioning fingers to bias the flexible elongate member toward or away from a plaque.

27. The method of claim 23, wherein the expansion means comprises an inflation seal.

28. The method of claim 27, wherein the flexible elongate member further includes an inflation system comprising a first lumen adapted to receive pressurized fluid and a second lumen adapted to evacuate gas, and wherein the inflation seal further includes an entry port in fluid communication with the first lumen of the elongate member and an exit port in fluid communication with the second lumen of the elongate member, so that when fluid is advanced through the first lumen, the fluid enters the inflation seal and forces gas from the inflation seal through the second lumen, thereby purging the system of gas.

29. The method of claim 23, wherein the step of excising plaque from the artery further includes the step of using transcranial doppler ultrasound for cerebral monitoring of emboli.

30. The method of claim 23, wherein the step of contacting the atherectomy assembly with the plaque includes the step of operating a steering mechanism to maneuver the atherectomy assembly toward a plaque.

31. The method of claim 23, wherein the step of excising plaque further includes the step of guiding excised plaque to a cavity in the elongate member, said cavity being adapted to receive and store plaque material.

32. The method of claim 31, further comprising the step of grinding or abrading excised plaque material.

33. The method of claim 31, further comprising the step of aspirating the excised plaque material.

34. The method of claim 23, wherein the step of introducing the distal region of the arterial catheter into a region of interest includes the step of introducing the catheter into a vessel selected from the group consisting of the aorta, common carotid artery, external and internal carotid arteries, brachiocephalic trunk, middle cerebral artery, anterior cerebral artery, posterior cerebral artery, vertebral artery, basilar artery, subclavian artery, brachial artery, axillary artery, iliac artery, renal artery, femoral artery, popliteal artery, celiac artery, superior mesenteric artery, inferior mesenteric artery, anterior tibial artery, and posterior tibial artery.

* * * * *